(12) United States Patent
Ortiz et al.

(10) Patent No.: US 8,192,350 B2
(45) Date of Patent: Jun. 5, 2012

(54) METHODS AND DEVICES FOR MEASURING IMPEDANCE IN A GASTRIC RESTRICTION SYSTEM

(75) Inventors: Mark S. Ortiz, Milford, OH (US); Daniel F. Dlugos, Jr., Middletown, OH (US); Amy L. Marcotte, Mason, OH (US); David N. Plescia, Cincinnati, OH (US); David C. Yates, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1165 days.

(21) Appl. No.: 12/020,867

(22) Filed: Jan. 28, 2008

(65) Prior Publication Data

US 2009/0192404 A1 Jul. 30, 2009

(51) Int. Cl.
*A61F 2/00* (2006.01)
*A61F 2/48* (2006.01)

(52) U.S. Cl. .......................................... 600/37; 606/151
(58) Field of Classification Search .................... 600/37, 600/593; 606/151
See application file for complete search history.

(56) References Cited

U.S. PATENT DOCUMENTS

| RE3,036 E | 7/1868 | Shunk |
|---|---|---|
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |

(Continued)

FOREIGN PATENT DOCUMENTS

CA 1059035 7/1979

(Continued)

OTHER PUBLICATIONS

Partial European Search Report, Application No. 09250222.8, Mailed Jul. 6, 2009, 7 pages.

(Continued)

*Primary Examiner* — John Lacyk
*Assistant Examiner* — Shannon Canty
(74) *Attorney, Agent, or Firm* — Nutter McClennen & Fish LLP

(57) ABSTRACT

Methods and devices are provided for gathering impedance data related to implantable restriction devices. In general, the methods and devices can enable patients, health care providers, and others to use gathered data as a feedback mechanism to non-invasively monitor efficacy of an implantable restriction device in a patient and to identify, modify, and/or prescribe a treatment plan for the patient considering the gathered data. Impedance data can be gathered and analyzed for tissue proximate to the restriction device, e.g., a fat pad between a gastric band and the patient's stomach. Electrodes in contact with the tissue can measure an impedance of the tissue, with the impedance between the electrodes changing as the tissue reduces in size (e.g., as fat cells shrink) and/or changes configuration.

22 Claims, 12 Drawing Sheets

U.S. PATENT DOCUMENTS

| | | |
|---|---|---|
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |
| 3,205,547 A | 9/1965 | Riekse |
| 3,208,255 A | 9/1965 | Burk |
| 3,209,570 A | 10/1965 | Hills |
| 3,221,468 A | 12/1965 | Casey |

| | | | | | | |
|---|---|---|---|---|---|---|
| 3,228,703 A | 1/1966 | Wilson | | 3,504,664 A | 4/1970 | Haddad |
| 3,229,684 A | 1/1966 | Nagumo et al. | | 3,505,808 A | 4/1970 | Eschle |
| 3,236,088 A | 2/1966 | Moller | | 3,509,754 A | 5/1970 | Massingill et al. |
| 3,238,624 A | 3/1966 | McCabe | | 3,512,517 A | 5/1970 | Kadish et al. |
| 3,240,510 A | 3/1966 | Spouge | | 3,514,919 A | 6/1970 | Ashton et al. |
| 3,245,642 A | 4/1966 | Dicke | | 3,516,220 A | 6/1970 | Buford et al. |
| 3,255,568 A | 6/1966 | Martin et al. | | 3,517,553 A | 6/1970 | Williams et al. |
| 3,260,091 A | 7/1966 | Shaw, Jr. | | 3,527,226 A | 9/1970 | Hakin et al. |
| 3,265,822 A | 8/1966 | Moulten | | 3,529,908 A | 9/1970 | Smith |
| 3,266,487 A | 8/1966 | Watkins et al. | | 3,530,449 A | 9/1970 | Anderson |
| 3,273,447 A | 9/1966 | Frank | | 3,533,403 A | 10/1970 | Woodson |
| 3,283,352 A | 11/1966 | Hu | | 3,534,728 A | 10/1970 | Barrows |
| 3,290,919 A | 12/1966 | Malinak et al. | | 3,534,872 A | 10/1970 | Roth et al. |
| 3,292,493 A | 12/1966 | Franklin | | 3,535,914 A | 10/1970 | Veith et al. |
| 3,292,888 A | 12/1966 | Fischer | | 3,539,009 A | 11/1970 | Kudlaty |
| 3,294,988 A | 12/1966 | Packard | | 3,543,744 A | 12/1970 | LePar |
| 3,299,603 A | 1/1967 | Shaw | | 3,545,275 A | 12/1970 | Harrison at al. |
| 3,299,882 A | 1/1967 | Masino | | 3,550,583 A | 12/1970 | Chiku |
| 3,301,514 A | 1/1967 | Sugaya | | 3,550,847 A | 12/1970 | Scott |
| 3,302,457 A | 2/1967 | Mayes | | 3,563,094 A | 2/1971 | Rieschel |
| 3,306,384 A | 2/1967 | Ross | | 3,563,245 A | 2/1971 | McLean et al. |
| 3,313,314 A | 4/1967 | Burke et al. | | 3,566,083 A | 2/1971 | McMillin |
| 3,316,935 A | 5/1967 | Kaiser et al. | | 3,566,875 A | 3/1971 | Stoehr |
| 3,320,750 A | 5/1967 | Haise et al. | | 3,568,367 A | 3/1971 | Myers |
| 3,321,035 A | 5/1967 | Tarpley | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding et al. | | 3,590,818 A | 7/1971 | Lemole |
| 3,353,481 A | 11/1967 | Antonucci | | 3,590,992 A | 7/1971 | Soderstrom et al. |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,242 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens et al. | | 3,633,881 A | 1/1972 | Yurdin |
| 3,396,561 A | 8/1968 | Day | | 3,635,061 A | 1/1972 | Rydell et al. |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth et al. | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,677,685 A | 7/1972 | Aoki et al. |
| 3,438,391 A | 4/1969 | Yocum | | 3,686,958 A | 8/1972 | Porter et al. |
| 3,443,608 A | 5/1969 | Copping et al. | | 3,688,568 A | 9/1972 | Karper et al. |
| 3,445,335 A | 5/1969 | Gluntz | | 3,701,392 A | 10/1972 | Wirth et al. |
| 3,447,281 A | 6/1969 | Bufford et al. | | 3,702,677 A | 11/1972 | Heffington |
| 3,450,153 A | 6/1969 | Hildebrandt et al. | | 3,703,099 A | 11/1972 | Rouse et al. |
| 3,453,546 A | 7/1969 | Fryer | | 3,712,138 A | 1/1973 | Alinari et al. |
| 3,453,848 A | 7/1969 | Williamson | | 3,713,124 A | 1/1973 | Durland et al. |
| 3,456,134 A | 7/1969 | Ko | | 3,719,524 A | 3/1973 | Ripley et al. |
| 3,457,909 A | 7/1969 | Laird | | 3,721,412 A | 3/1973 | Kindorf |
| 3,460,557 A | 8/1969 | Gallant | | 3,723,247 A | 3/1973 | Leine et al. |
| 3,463,338 A | 8/1969 | Schneider | | 3,724,000 A | 4/1973 | Eakman |
| 3,469,818 A | 9/1969 | Cowan | | 3,727,463 A | 4/1973 | Intraub |
| 3,470,725 A | 10/1969 | Brown et al. | | 3,727,616 A | 4/1973 | Lenzkes |
| 3,472,230 A | 10/1969 | Fogarty | | 3,730,174 A | 5/1973 | Madison |
| 3,478,344 A | 11/1969 | Schwitzgebel et al. | | 3,730,560 A | 5/1973 | Abildgaard et al. |
| 3,482,449 A | 12/1969 | Werner | | 3,731,679 A | 5/1973 | Wilhelmson et al. |
| 3,482,816 A | 12/1969 | Arnold | | 3,731,681 A | 5/1973 | Blackshear et al. |
| 3,487,959 A | 1/1970 | Pearne et al. | | 3,732,731 A | 5/1973 | Fussell, Jr. |
| 3,491,842 A | 1/1970 | Delacour et al. | | 3,735,040 A | 5/1973 | Punt et al. |
| 3,492,638 A | 1/1970 | Lane | | 3,736,930 A | 6/1973 | Georgi |
| 3,502,829 A | 3/1970 | Reynolds | | 3,738,356 A | 6/1973 | Workman |
| 3,503,116 A | 3/1970 | Strack | | 3,740,921 A | 6/1973 | Meyer et al. |

| | | | | | |
|---|---|---|---|---|---|
| 3,746,111 A | 7/1973 | Berthiaume et al. | 3,920,965 A | 11/1975 | Sohrwardy et al. |
| 3,748,678 A | 7/1973 | Ballou | 3,921,682 A | 11/1975 | McGahey et al. |
| 3,749,098 A | 7/1973 | De Bennetot | 3,922,951 A | 12/1975 | Linsinger et al. |
| 3,749,422 A | 7/1973 | Abildgaard et al. | 3,923,060 A | 12/1975 | Ellinwood, Jr. |
| 3,749,423 A | 7/1973 | Abildgaard et al. | 3,924,635 A | 12/1975 | Hakim et al. |
| 3,750,194 A | 8/1973 | Summers | 3,928,980 A | 12/1975 | Ganzinotti et al. |
| 3,757,770 A | 9/1973 | Brayshaw et al. | 3,929,175 A | 12/1975 | Coone |
| 3,759,095 A | 9/1973 | Short, Jr. et al. | 3,930,682 A | 1/1976 | Booth |
| 3,760,638 A | 9/1973 | Lawson et al. | 3,930,852 A | 1/1976 | Tanaka et al. |
| 3,763,960 A | 10/1973 | John et al. | 3,936,028 A | 2/1976 | Norton et al. |
| 3,765,142 A | 10/1973 | Lindquist et al. | 3,940,122 A | 2/1976 | Janzen et al. |
| 3,765,494 A | 10/1973 | Kielman, Jr. | 3,940,630 A | 2/1976 | Bergonz |
| 3,769,156 A | 10/1973 | Brecy et al. | 3,942,299 A | 3/1976 | Bory et al. |
| 3,769,830 A | 11/1973 | Porter et al. | 3,942,382 A | 3/1976 | Hok et al. |
| 3,774,243 A | 11/1973 | Ng et al. | 3,942,516 A | 3/1976 | Glynn et al. |
| 3,776,333 A | 12/1973 | Mathauser | 3,942,536 A | 3/1976 | Mirowski et al. |
| 3,778,051 A | 12/1973 | Allen et al. | 3,943,915 A | 3/1976 | Severson |
| 3,780,578 A | 12/1973 | Sellman et al. | 3,945,704 A | 3/1976 | Kraus et al. |
| 3,781,902 A | 12/1973 | Shim et al. | 3,946,613 A | 3/1976 | Silver |
| 3,783,585 A | 1/1974 | Hoyland | 3,946,615 A | 3/1976 | Hluchan |
| 3,789,667 A | 2/1974 | Porter et al. | 3,946,724 A | 3/1976 | La Balme et al. |
| 3,796,095 A | 3/1974 | Fussell, Jr. | 3,948,141 A | 4/1976 | Shinjo et al. |
| 3,807,219 A | 4/1974 | Wallskog | 3,949,388 A | 4/1976 | Fuller |
| 3,811,429 A | 5/1974 | Fletcher et al. | 3,953,289 A | 4/1976 | Costes et al. |
| 3,815,722 A | 6/1974 | Sessoms | 3,954,271 A | 5/1976 | Tredway, Sr. |
| 3,818,765 A | 6/1974 | Eriksen et al. | 3,958,558 A | 5/1976 | Dunphy et al. |
| 3,820,400 A | 6/1974 | Russo | 3,961,425 A | 6/1976 | Swanson et al. |
| 3,820,795 A | 6/1974 | Taylor | 3,961,646 A | 6/1976 | Schon et al. |
| 3,823,610 A | 7/1974 | Fussell, Jr. | 3,962,895 A | 6/1976 | Rydell et al. |
| 3,825,065 A | 7/1974 | Lloyd et al. | 3,962,921 A | 6/1976 | Lips |
| 3,825,963 A | 7/1974 | Abildgaard et al. | 3,963,019 A | 6/1976 | Quandt |
| 3,825,964 A | 7/1974 | Groswith, III et al. | 3,964,485 A | 6/1976 | Neumeier |
| 3,828,672 A | 8/1974 | Gazzola et al. | 3,964,770 A | 6/1976 | Abildgaard et al. |
| 3,828,766 A | 8/1974 | Krasnow | 3,967,737 A | 7/1976 | Peralta et al. |
| 3,831,588 A | 8/1974 | Rindner | 3,968,473 A | 7/1976 | Patton et al. |
| 3,831,942 A | 8/1974 | Del Mar | 3,968,694 A | 7/1976 | Clark |
| 3,833,238 A | 9/1974 | Liard et al. | 3,972,320 A | 8/1976 | Kalman |
| 3,834,167 A | 9/1974 | Tabor | 3,973,753 A | 8/1976 | Wheeler |
| 3,834,739 A | 9/1974 | Abildgaard et al. | 3,973,858 A | 8/1976 | Poisson et al. |
| 3,835,523 A | 9/1974 | Stansfield et al. | 3,974,655 A | 8/1976 | Halpern et al. |
| 3,839,708 A | 10/1974 | Bredesen et al. | 3,974,865 A | 8/1976 | Fenton et al. |
| 3,842,483 A | 10/1974 | Cramer | 3,977,391 A | 8/1976 | Fleischmann |
| 3,842,668 A | 10/1974 | Lippke et al. | 3,980,871 A | 9/1976 | Lindstrom et al. |
| 3,845,664 A | 11/1974 | Perry, Jr. | 3,982,571 A | 9/1976 | Fenton et al. |
| 3,845,751 A | 11/1974 | Runstetler | 3,983,948 A | 10/1976 | Jeter |
| 3,845,757 A | 11/1974 | Weyer | 3,985,133 A | 10/1976 | Jenkins et al. |
| 3,847,434 A | 11/1974 | Weman et al. | 3,987,860 A | 10/1976 | Jabsen |
| 3,850,208 A | 11/1974 | Hamilton | 3,989,005 A | 11/1976 | Bowler, Jr. et al. |
| 3,853,117 A | 12/1974 | Murr | 3,991,749 A | 11/1976 | Zent |
| 3,854,469 A | 12/1974 | Giori et al. | 3,992,948 A | 11/1976 | D'Antonio et al. |
| 3,855,902 A | 12/1974 | Kirst et al. | 3,993,149 A | 11/1976 | Harvey |
| 3,857,399 A | 12/1974 | Zacouto et al. | 3,996,927 A | 12/1976 | Frank |
| 3,857,452 A | 12/1974 | Hartman | 3,996,962 A | 12/1976 | Sutherland |
| 3,857,745 A | 12/1974 | Grausch et al. | 4,003,141 A | 1/1977 | Le Roy |
| 3,858,581 A | 1/1975 | Kamen | 4,005,282 A | 1/1977 | Jennings |
| 3,863,622 A | 2/1975 | Buuck | 4,005,593 A | 2/1977 | Goldberg |
| 3,863,933 A | 2/1975 | Tredway | 4,006,735 A | 2/1977 | Hittman et al. |
| 3,867,950 A | 2/1975 | Fischell | 4,009,375 A | 2/1977 | White et al. |
| 3,868,008 A | 2/1975 | Brumbaugh | 4,009,591 A | 3/1977 | Hester |
| 3,868,679 A | 2/1975 | Arneson | 4,010,449 A | 3/1977 | Faggin et al. |
| 3,871,599 A | 3/1975 | Takada et al. | 4,014,319 A | 3/1977 | Favre et al. |
| 3,872,285 A | 3/1975 | Shum et al. | 4,014,321 A | 3/1977 | March |
| 3,874,388 A | 4/1975 | King et al. | 4,016,764 A | 4/1977 | Rice |
| 3,876,980 A | 4/1975 | Haemmig et al. | 4,017,329 A | 4/1977 | Larson |
| 3,878,908 A | 4/1975 | Andersson et al. | 4,018,134 A | 4/1977 | Linsinger et al. |
| 3,881,528 A | 5/1975 | Mackenzie | 4,022,190 A | 5/1977 | Meyer |
| 3,893,111 A | 7/1975 | Cotter | 4,024,864 A | 5/1977 | Davies et al. |
| 3,893,451 A | 7/1975 | Durand et al. | 4,025,912 A | 5/1977 | Rice |
| 3,895,681 A | 7/1975 | Griffin et al. | 4,026,276 A | 5/1977 | Chubbuck |
| 3,899,862 A | 8/1975 | Muys et al. | 4,027,661 A | 6/1977 | Lyon et al. |
| 3,904,234 A | 9/1975 | Hill et al. | 4,031,899 A | 6/1977 | Renirie et al. |
| 3,908,334 A | 9/1975 | Rychiger et al. | 4,036,775 A | 7/1977 | Trautvetter et al. |
| 3,908,461 A | 9/1975 | Turpen | 4,039,069 A | 8/1977 | Kwan et al. |
| 3,908,721 A | 9/1975 | McGahey et al. | 4,041,954 A | 8/1977 | Ohara et al. |
| 3,910,087 A | 10/1975 | Jones | 4,042,504 A | 8/1977 | Drori et al. |
| 3,912,168 A | 10/1975 | Mullins et al. | 4,045,345 A | 8/1977 | Drori et al. |
| 3,912,304 A | 10/1975 | Abildgaard et al. | 4,047,851 A | 9/1977 | Bender |
| 3,918,286 A | 11/1975 | Whitehead | 4,048,494 A | 9/1977 | Liesting et al. |
| 3,918,291 A | 11/1975 | Pauly et al. | 4,048,879 A | 9/1977 | Cox |

| | | | | | | |
|---|---|---|---|---|---|---|
| 4,049,004 A | 9/1977 | Walters | | 4,186,749 A | 2/1980 | Fryer |
| 4,051,338 A | 9/1977 | Harris, III | | 4,186,751 A | 2/1980 | Fleischmann |
| 4,052,991 A | 10/1977 | Zacouto et al. | | 4,190,057 A | 2/1980 | Hill et al. |
| 4,055,074 A | 10/1977 | Thimons et al. | | 4,191,004 A | 3/1980 | Gmuer et al. |
| 4,055,175 A | 10/1977 | Clemens et al. | | 4,191,187 A | 3/1980 | Wright et al. |
| 4,056,854 A | 11/1977 | Boretos et al. | | 4,192,192 A | 3/1980 | Schnell |
| 4,058,007 A | 11/1977 | Exner et al. | | 4,193,397 A | 3/1980 | Tucker et al. |
| 4,062,351 A | 12/1977 | Hastwell et al. | | 4,204,547 A | 5/1980 | Allocca |
| 4,062,354 A | 12/1977 | Taylor et al. | | 4,206,755 A | 6/1980 | Klein et al. |
| 4,062,360 A | 12/1977 | Bentley | | 4,206,761 A | 6/1980 | Cosman |
| 4,063,439 A | 12/1977 | Besson et al. | | 4,206,762 A | 6/1980 | Cosman |
| 4,064,882 A | 12/1977 | Johnson et al. | | 4,207,903 A | 6/1980 | O'Neill |
| 4,070,239 A | 1/1978 | Bevilacqua | | 4,212,074 A | 7/1980 | Kuno et al. |
| 4,072,047 A | 2/1978 | Reismuller et al. | | 4,217,221 A | 8/1980 | Masso |
| 4,073,292 A | 2/1978 | Edelman | | 4,217,588 A | 8/1980 | Freeny, Jr. |
| 4,075,099 A | 2/1978 | Pelton et al. | | 4,220,189 A | 9/1980 | Marquez |
| 4,075,602 A | 2/1978 | Clothier | | 4,221,219 A | 9/1980 | Tucker |
| 4,077,072 A | 3/1978 | Dezura et al. | | 4,221,523 A | 9/1980 | Eberle |
| 4,077,394 A | 3/1978 | McCurdy | | 4,222,377 A | 9/1980 | Burton |
| 4,077,405 A | 3/1978 | Haerten et al. | | 4,223,837 A | 9/1980 | Gubbiotti et al. |
| 4,077,882 A | 3/1978 | Gangemi | | 4,226,124 A | 10/1980 | Kersten et al. |
| 4,078,620 A | 3/1978 | Westlake et al. | | 4,226,229 A | 10/1980 | Eckhart et al. |
| 4,080,653 A | 3/1978 | Barnes, Jr. et al. | | 4,227,533 A | 10/1980 | Godfrey |
| 4,084,752 A | 4/1978 | Hagiwara et al. | | 4,231,376 A | 11/1980 | Lyon et al. |
| 4,086,488 A | 4/1978 | Hill | | 4,232,682 A | 11/1980 | Veth |
| 4,087,568 A | 5/1978 | Fay et al. | | 4,237,900 A | 12/1980 | Schulman et al. |
| 4,088,417 A | 5/1978 | Kosmowski | | 4,241,247 A | 12/1980 | Byrne et al. |
| 4,089,329 A | 5/1978 | Couvillon, Jr. et al. | | 4,241,870 A | 12/1980 | Marcus |
| 4,090,802 A | 5/1978 | Bilz et al. | | 4,245,593 A | 1/1981 | Stein |
| 4,092,719 A | 5/1978 | Salmon et al. | | 4,246,877 A | 1/1981 | Kennedy |
| 4,092,925 A | 6/1978 | Fromson | | 4,247,850 A | 1/1981 | Marcus |
| 4,096,866 A | 6/1978 | Fischell | | 4,248,238 A | 2/1981 | Joseph et al. |
| 4,098,293 A | 7/1978 | Kramer et al. | | 4,248,241 A | 2/1981 | Tacchi |
| 4,103,496 A | 8/1978 | Colamussi et al. | | 4,256,094 A | 3/1981 | Kapp et al. |
| 4,106,370 A | 8/1978 | Kraus et al. | | 4,256,118 A | 3/1981 | Nagel et al. |
| 4,107,689 A | 8/1978 | Jellinek | | 4,262,343 A | 4/1981 | Claycomb |
| 4,107,995 A | 8/1978 | Ligman et al. | | 4,262,632 A | 4/1981 | Hanton et al. |
| 4,108,148 A | 8/1978 | Cannon, III | | 4,265,241 A | 5/1981 | Portner et al. |
| 4,108,575 A | 8/1978 | Schal et al. | | 4,265,252 A | 5/1981 | Chubbuck et al. |
| 4,109,148 A | 8/1978 | Jaulmes et al. | | 4,271,018 A | 6/1981 | Drori et al. |
| 4,109,518 A | 8/1978 | Dooley et al. | | 4,273,070 A | 6/1981 | Hoefelmayr et al. |
| 4,109,644 A | 8/1978 | Kojima | | 4,274,444 A | 6/1981 | Ruyak |
| 4,111,056 A | 9/1978 | Mastromatteo | | 4,275,600 A | 6/1981 | Turner et al. |
| 4,111,629 A | 9/1978 | Nussbaumer et al. | | 4,275,913 A | 6/1981 | Marcus |
| 4,114,424 A | 9/1978 | Johnson | | 4,278,540 A | 7/1981 | Drori et al. |
| 4,114,606 A | 9/1978 | Seylar | | 4,280,036 A | 7/1981 | Fukatsu et al. |
| 4,120,097 A | 10/1978 | Jeter | | 4,280,775 A | 7/1981 | Wood |
| 4,120,134 A | 10/1978 | Scholle | | 4,281,666 A | 8/1981 | Cosman |
| 4,121,635 A | 10/1978 | Hansel | | 4,281,667 A | 8/1981 | Cosman |
| 4,123,310 A | 10/1978 | Varon et al. | | 4,284,073 A | 8/1981 | Krause et al. |
| 4,124,023 A | 11/1978 | Fleischmann et al. | | 4,285,770 A | 8/1981 | Chi et al. |
| 4,127,110 A | 11/1978 | Bullara | | 4,291,699 A | 9/1981 | Geddes et al. |
| 4,130,169 A | 12/1978 | Denison | | 4,295,963 A | 10/1981 | Drori et al. |
| 4,131,596 A | 12/1978 | Allen | | 4,297,927 A | 11/1981 | Kuroda et al. |
| 4,133,355 A | 1/1979 | Mayer | | 4,303,075 A | 12/1981 | Heilman et al. |
| 4,133,367 A | 1/1979 | Abell | | 4,305,402 A | 12/1981 | Katims |
| 4,140,131 A | 2/1979 | Dutcher et al. | | 4,312,374 A | 1/1982 | Drori et al. |
| 4,141,348 A | 2/1979 | Hittman | | 4,314,480 A | 2/1982 | Becker |
| 4,141,349 A | 2/1979 | Ory et al. | | 4,316,693 A | 2/1982 | Baxter et al. |
| 4,143,661 A | 3/1979 | LaForge et al. | | 4,325,387 A | 4/1982 | Helfer |
| 4,146,029 A | 3/1979 | Ellinwood, Jr. | | 4,327,804 A | 5/1982 | Reed |
| 4,147,161 A | 4/1979 | Ikebe et al. | | 4,328,654 A | 5/1982 | Van Ginkel et al. |
| 4,148,096 A | 4/1979 | Haas et al. | | 4,332,254 A | 6/1982 | Lundquist |
| 4,149,423 A | 4/1979 | Frosch et al. | | 4,339,831 A | 7/1982 | Johnson |
| 4,151,823 A | 5/1979 | Grosse et al. | | 4,342,218 A | 8/1982 | Fox |
| 4,153,085 A | 5/1979 | Adams | | 4,342,308 A | 8/1982 | Trick |
| 4,156,422 A | 5/1979 | Hildebrandt et al. | | 4,346,604 A | 8/1982 | Snook et al. |
| 4,160,448 A | 7/1979 | Jackson | | 4,347,851 A | 9/1982 | Jundanian |
| 4,160,971 A | 7/1979 | Jones et al. | | 4,350,647 A | 9/1982 | de la Cruz |
| 4,166,469 A | 9/1979 | Littleford | | 4,350,970 A | 9/1982 | von Tomkewitsch et al. |
| 4,167,304 A | 9/1979 | Gelbke | | 4,351,037 A | 9/1982 | Scherbatskoy |
| 4,167,952 A | 9/1979 | Reinicke | | 4,351,116 A | 9/1982 | Scott, Jr. |
| 4,168,567 A | 9/1979 | Leguy et al. | | 4,356,486 A | 10/1982 | Mount |
| 4,170,280 A | 10/1979 | Schwarz | | 4,360,010 A | 11/1982 | Finney |
| 4,171,218 A | 10/1979 | Hoshino et al. | | 4,360,277 A | 11/1982 | Daniel et al. |
| 4,183,124 A | 1/1980 | Hoffman | | 4,361,153 A | 11/1982 | Slocum et al. |
| 4,183,247 A | 1/1980 | Allen et al. | | 4,363,236 A | 12/1982 | Meyers |
| 4,185,641 A | 1/1980 | Minior et al. | | 4,364,276 A | 12/1982 | Shimazoe et al. |
| 4,186,287 A | 1/1980 | Scott | | 4,365,425 A | 12/1982 | Gotchel |

| | | | | | | |
|---|---|---|---|---|---|---|
| 4,368,937 | A | 1/1983 | Palombo et al. | 4,497,201 A | 2/1985 | Allen et al. |
| 4,369,013 | A | 1/1983 | Abildgaard et al. | 4,499,394 A | 2/1985 | Koal |
| 4,373,527 | A | 2/1983 | Fischell | 4,499,691 A | 2/1985 | Karazim et al. |
| 4,376,523 | A | 3/1983 | Goyen et al. | 4,499,750 A | 2/1985 | Gerber et al. |
| 4,378,809 | A | 4/1983 | Cosman | 4,503,678 A | 3/1985 | Wimbush et al. |
| 4,380,427 | A | 4/1983 | Hehl et al. | 4,511,974 A | 4/1985 | Nakane et al. |
| 4,385,636 | A | 5/1983 | Cosman | 4,513,295 A | 4/1985 | Jones et al. |
| 4,386,422 | A | 5/1983 | Mumby et al. | 4,515,004 A | 5/1985 | Jaenson |
| 4,387,907 | A | 6/1983 | Hiestand et al. | 4,515,750 A | 5/1985 | Pardini et al. |
| 4,392,368 | A | 7/1983 | Folkesson et al. | 4,516,866 A | 5/1985 | Yamauchi et al. |
| 4,393,899 | A | 7/1983 | Tsuji et al. | 4,518,637 A | 5/1985 | Takeda et al. |
| 4,393,951 | A | 7/1983 | Horst-Rudolf et al. | 4,519,401 A | 5/1985 | Ko et al. |
| 4,395,232 | A | 7/1983 | Koch | 4,520,443 A | 5/1985 | Yuki et al. |
| 4,395,258 | A | 7/1983 | Wang et al. | 4,522,213 A | 6/1985 | Wallroth et al. |
| 4,395,916 | A | 8/1983 | Martin | 4,527,568 A | 7/1985 | Rickards et al. |
| 4,398,983 | A | 8/1983 | Suzuki et al. | 4,529,401 A | 7/1985 | Leslie et al. |
| 4,399,705 | A | 8/1983 | Weiger et al. | 4,531,526 A | 7/1985 | Genest |
| 4,399,707 | A | 8/1983 | Wamstad | 4,531,936 A | 7/1985 | Gordon |
| 4,399,809 | A | 8/1983 | Baro et al. | 4,536,000 A | 8/1985 | Rohm et al. |
| 4,399,821 | A | 8/1983 | Bowers | 4,537,005 A | 8/1985 | Hoyland et al. |
| 4,403,984 | A | 9/1983 | Ash et al. | 4,537,129 A | 8/1985 | Heinemann et al. |
| 4,404,968 | A | 9/1983 | Evans, Sr. | 4,538,616 A | 9/1985 | Rogoff |
| 4,404,974 | A | 9/1983 | Titus | 4,540,404 A | 9/1985 | Wolvek |
| 4,405,318 | A | 9/1983 | Whitney et al. | 4,542,461 A | 9/1985 | Eldridge et al. |
| 4,407,125 | A | 10/1983 | Parsons et al. | 4,544,369 A | 10/1985 | Skakoon et al. |
| 4,407,271 | A | 10/1983 | Schiff | 4,545,185 A | 10/1985 | Chikatani et al. |
| 4,407,296 | A | 10/1983 | Anderson | 4,546,524 A | 10/1985 | Kreft |
| 4,407,326 | A | 10/1983 | Wilhelm | 4,548,209 A | 10/1985 | Wielders et al. |
| 4,408,597 | A | 10/1983 | Tenney, Jr. | 4,552,150 A | 11/1985 | Zacouto et al. |
| 4,408,615 | A | 10/1983 | Grossman | 4,553,226 A | 11/1985 | Scherbatskoy |
| 4,415,071 | A | 11/1983 | Butler et al. | 4,556,063 A | 12/1985 | Thompson et al. |
| 4,416,282 | A | 11/1983 | Saulson et al. | 4,557,269 A | 12/1985 | Reynolds et al. |
| 4,418,899 | A | 12/1983 | Zimmermann et al. | 4,557,332 A | 12/1985 | Denison et al. |
| 4,419,393 | A | 12/1983 | Hanson et al. | 4,559,815 A | 12/1985 | Needham et al. |
| 4,421,505 | A | 12/1983 | Schwartz | 4,560,979 A | 12/1985 | Rosskopf et al. |
| 4,424,720 | A | 1/1984 | Bucchianeri | 4,561,442 A | 12/1985 | Vollmann et al. |
| 4,428,228 | A | 1/1984 | Banzhaf et al. | 4,562,751 A | 1/1986 | Nason et al. |
| 4,428,365 | A | 1/1984 | Hakky et al. | 4,563,175 A | 1/1986 | LaFond |
| 4,430,899 | A | 2/1984 | Wessel et al. | 4,565,116 A | 1/1986 | Hehl et al. |
| 4,431,009 | A | 2/1984 | Marino, Jr. et al. | 4,566,456 A | 1/1986 | Koning et al. |
| 4,431,365 | A | 2/1984 | Sturtz, Jr. | 4,569,623 A | 2/1986 | Goldmann |
| 4,432,363 | A | 2/1984 | Kakegawa et al. | 4,570,351 A | 2/1986 | Szanto et al. |
| 4,435,173 | A | 3/1984 | Siposs et al. | 4,571,161 A | 2/1986 | Leblanc et al. |
| 4,439,186 | A | 3/1984 | Kuhl et al. | 4,571,995 A | 2/1986 | Timme |
| 4,441,491 | A | 4/1984 | Evans, Sr. | 4,573,835 A | 3/1986 | Eckardt et al. |
| 4,441,501 | A | 4/1984 | Parent | 4,574,792 A | 3/1986 | Trick |
| 4,444,194 | A | 4/1984 | Burcham | 4,576,181 A | 3/1986 | Wallace et al. |
| 4,444,498 | A | 4/1984 | Heinemann | 4,576,183 A | 3/1986 | Plicchi et al. |
| 4,445,385 | A | 5/1984 | Endo | 4,577,512 A | 3/1986 | Lowenheck et al. |
| 4,446,711 | A | 5/1984 | Valente | 4,581,018 A | 4/1986 | Jassawalla et al. |
| 4,447,224 | A | 5/1984 | DeCant, Jr. et al. | 4,581,915 A | 4/1986 | Haulsee et al. |
| 4,449,493 | A | 5/1984 | Kopec et al. | 4,587,840 A | 5/1986 | Dobler et al. |
| 4,450,811 | A | 5/1984 | Ichikawa et al. | 4,589,805 A | 5/1986 | Duffner et al. |
| 4,451,033 | A | 5/1984 | Nestegard | 4,592,339 A | 6/1986 | Kuzmak et al. |
| 4,453,537 | A | 6/1984 | Spitzer | 4,592,340 A | 6/1986 | Boyles |
| 4,453,578 | A | 6/1984 | Wilder | 4,593,703 A | 6/1986 | Cosman |
| 4,460,835 | A | 7/1984 | Masuoka et al. | 4,595,228 A | 6/1986 | Chu |
| 4,464,170 | A | 8/1984 | Clemens et al. | 4,596,563 A | 6/1986 | Pande |
| 4,465,015 | A | 8/1984 | Osta et al. | 4,599,943 A | 7/1986 | Kobler et al. |
| 4,465,474 | A | 8/1984 | Mardorf et al. | 4,600,855 A | 7/1986 | Strachan et al. |
| 4,466,290 | A | 8/1984 | Frick | 4,602,541 A | 7/1986 | Benzinger et al. |
| 4,468,172 | A | 8/1984 | Dixon et al. | 4,604,089 A | 8/1986 | Santangelo et al. |
| 4,468,762 | A | 8/1984 | Jurgens et al. | 4,605,354 A | 8/1986 | Daly |
| 4,469,365 | A | 9/1984 | Marcus et al. | 4,606,419 A | 8/1986 | Perini |
| 4,471,182 | A | 9/1984 | Wielgos et al. | 4,606,478 A | 8/1986 | Hack et al. |
| 4,471,786 | A | 9/1984 | Inagaki et al. | 4,610,256 A | 9/1986 | Wallace |
| 4,473,067 | A | 9/1984 | Schiff | 4,614,137 A | 9/1986 | Jones |
| 4,473,078 | A | 9/1984 | Angel | 4,617,016 A | 10/1986 | Blomberg et al. |
| 4,476,721 | A | 10/1984 | Hochreuther et al. | 4,618,861 A | 10/1986 | Gettens et al. |
| 4,478,213 | A | 10/1984 | Redding | 4,620,807 A | 11/1986 | Polit |
| 4,478,538 | A | 10/1984 | Kakino et al. | 4,621,331 A | 11/1986 | Iwata et al. |
| 4,483,196 | A | 11/1984 | Kurtz et al. | 4,622,871 A | 11/1986 | Van Sickle et al. |
| 4,484,135 | A | 11/1984 | Ishihara et al. | 4,626,462 A | 12/1986 | Kober et al. |
| 4,485,813 | A | 12/1984 | Anderson et al. | 4,633,304 A | 12/1986 | Nagasaki et al. |
| 4,489,916 | A | 12/1984 | Stevens | 4,633,878 A | 1/1987 | Bombardieri et al. |
| 4,492,632 | A | 1/1985 | Mattson | 4,635,182 A | 1/1987 | Hintz |
| 4,494,411 | A | 1/1985 | Koschke et al. | 4,637,736 A | 1/1987 | Andeen et al. |
| 4,494,950 | A | 1/1985 | Fischell | 4,638,665 A | 1/1987 | Benson et al. |
| 4,497,176 | A | 2/1985 | Rubin et al. | 4,644,246 A | 2/1987 | Knapen et al. |

| | | |
|---|---|---|
| 4,646,553 A | 3/1987 | Tufte et al. |
| 4,648,363 A | 3/1987 | Kronich |
| 4,648,406 A | 3/1987 | Miller |
| 4,658,358 A | 4/1987 | Leach et al. |
| 4,658,760 A | 4/1987 | Zebuhr |
| 4,660,568 A | 4/1987 | Cosman |
| 4,665,511 A | 5/1987 | Rodney et al. |
| 4,665,896 A | 5/1987 | LaForge et al. |
| 4,669,484 A | 6/1987 | Masters |
| 4,672,974 A | 6/1987 | Lee |
| 4,674,457 A | 6/1987 | Berger et al. |
| 4,674,546 A | 6/1987 | Fournier et al. |
| 4,678,408 A | 7/1987 | Nason et al. |
| 4,681,559 A | 7/1987 | Hooven |
| 4,683,850 A | 8/1987 | Bauder et al. |
| 4,685,463 A | 8/1987 | Williams |
| 4,685,469 A | 8/1987 | Keller et al. |
| 4,685,903 A | 8/1987 | Cable et al. |
| 4,686,987 A | 8/1987 | Salo et al. |
| 4,687,530 A | 8/1987 | Berscheid et al. |
| 4,689,979 A | 9/1987 | Otsuka et al. |
| 4,691,694 A | 9/1987 | Boyd et al. |
| 4,691,710 A | 9/1987 | Dickens et al. |
| 4,693,253 A | 9/1987 | Adams |
| 4,695,237 A | 9/1987 | Inaba et al. |
| 4,696,189 A | 9/1987 | Hochreuther et al. |
| 4,697,574 A | 10/1987 | Karcher et al. |
| 4,698,038 A | 10/1987 | Key et al. |
| 4,700,497 A | 10/1987 | Sato et al. |
| 4,700,610 A | 10/1987 | Bauer et al. |
| 4,701,143 A | 10/1987 | Key et al. |
| 4,703,756 A | 11/1987 | Gough et al. |
| 4,705,507 A | 11/1987 | Boyles |
| 4,706,948 A | 11/1987 | Kroecher et al. |
| 4,712,562 A | 12/1987 | Ohayon et al. |
| 4,718,425 A | 1/1988 | Tanaka et al. |
| 4,722,348 A | 2/1988 | Ligtenberg et al. |
| 4,724,806 A | 2/1988 | Hartwig et al. |
| 4,724,830 A | 2/1988 | Fischell |
| 4,725,826 A | 2/1988 | Hunter |
| 4,728,479 A | 3/1988 | Merkovsky |
| 4,729,517 A | 3/1988 | Krokor et al. |
| 4,730,188 A | 3/1988 | Milheiser |
| 4,730,420 A | 3/1988 | Stratmann et al. |
| 4,730,619 A | 3/1988 | Koning et al. |
| 4,731,058 A | 3/1988 | Doan |
| 4,735,205 A | 4/1988 | Chachques et al. |
| 4,738,267 A | 4/1988 | Lazorthes et al. |
| 4,738,268 A | 4/1988 | Kipnis |
| 4,741,345 A | 5/1988 | Matthews et al. |
| 4,741,732 A | 5/1988 | Crankshaw et al. |
| 4,743,129 A | 5/1988 | Keryhuel et al. |
| 4,745,541 A | 5/1988 | Vaniglia et al. |
| 4,746,830 A | 5/1988 | Holland |
| 4,750,495 A | 6/1988 | Moore et al. |
| 4,752,115 A | 6/1988 | Murray, Jr. et al. |
| 4,752,658 A | 6/1988 | Mack |
| 4,757,463 A | 7/1988 | Ballou et al. |
| 4,759,386 A | 7/1988 | Grouw, III |
| 4,763,649 A | 8/1988 | Merrick |
| 4,765,001 A | 8/1988 | Smith |
| 4,767,406 A | 8/1988 | Wadham et al. |
| 4,769,001 A | 9/1988 | Prince |
| 4,772,896 A | 9/1988 | Nakatsu et al. |
| 4,773,401 A | 9/1988 | Citak et al. |
| 4,774,950 A | 10/1988 | Cohen |
| 4,774,955 A | 10/1988 | Jones |
| 4,777,953 A | 10/1988 | Ash et al. |
| 4,779,626 A | 10/1988 | Peel et al. |
| 4,781,192 A | 11/1988 | Demer |
| 4,782,826 A | 11/1988 | Fogarty |
| 4,783,106 A | 11/1988 | Nutter |
| 4,788,847 A | 12/1988 | Sterghos |
| 4,791,318 A | 12/1988 | Lewis et al. |
| 4,794,803 A | 1/1989 | Osterhout et al. |
| 4,796,641 A | 1/1989 | Mills et al. |
| 4,798,211 A | 1/1989 | Goor et al. |
| 4,798,227 A | 1/1989 | Goodwin |
| 4,799,491 A | 1/1989 | Eckerle |
| 4,799,625 A | 1/1989 | Weaver, Jr. et al. |
| 4,802,488 A | 2/1989 | Eckerle |
| 4,803,987 A | 2/1989 | Calfee et al. |
| 4,804,368 A | 2/1989 | Skakoon et al. |
| 4,807,321 A | 2/1989 | Grasselli et al. |
| 4,808,167 A | 2/1989 | Mann et al. |
| 4,812,823 A | 3/1989 | Dickerson |
| 4,819,656 A | 4/1989 | Spector |
| 4,820,265 A | 4/1989 | DeSatnick et al. |
| 4,820,953 A | 4/1989 | Saubolle et al. |
| 4,821,167 A | 4/1989 | Wiebe |
| 4,821,723 A | 4/1989 | Baker, Jr. et al. |
| 4,823,779 A | 4/1989 | Daly et al. |
| 4,830,006 A | 5/1989 | Haluska et al. |
| 4,832,034 A | 5/1989 | Pizziconi et al. |
| 4,833,384 A | 5/1989 | Munro et al. |
| 4,834,731 A | 5/1989 | Nowak et al. |
| 4,838,857 A | 6/1989 | Strowe et al. |
| 4,840,068 A | 6/1989 | Mayhew, Jr. |
| 4,840,350 A | 6/1989 | Cook et al. |
| 4,844,002 A | 7/1989 | Yasui et al. |
| 4,846,153 A | 7/1989 | Berci |
| 4,846,191 A | 7/1989 | Brockway et al. |
| 4,846,664 A | 7/1989 | Hehl et al. |
| 4,854,328 A | 8/1989 | Pollack |
| 4,863,470 A | 9/1989 | Carter |
| 4,865,587 A | 9/1989 | Walling |
| 4,867,160 A | 9/1989 | Schaldach et al. |
| 4,867,498 A | 9/1989 | Delphia et al. |
| 4,867,618 A | 9/1989 | Brohammer |
| 4,869,252 A | 9/1989 | Gilli |
| 4,870,258 A | 9/1989 | Mochizuki et al. |
| 4,871,351 A | 10/1989 | Feingold et al. |
| 4,872,483 A | 10/1989 | Shah |
| 4,872,869 A | 10/1989 | Johns |
| 4,873,677 A | 10/1989 | Sakamoto et al. |
| 4,875,483 A | 10/1989 | Vollmann et al. |
| 4,880,004 A | 11/1989 | Baker, Jr. et al. |
| 4,882,678 A | 11/1989 | Hollis et al. |
| 4,886,392 A | 12/1989 | Iio et al. |
| 4,895,151 A | 1/1990 | Grevis et al. |
| 4,896,594 A | 1/1990 | Baur et al. |
| 4,898,158 A | 2/1990 | Daly et al. |
| 4,898,578 A | 2/1990 | Rubalcaba, Jr. |
| 4,899,751 A | 2/1990 | Cohen |
| 4,899,752 A | 2/1990 | Cohen |
| 4,902,277 A | 2/1990 | Mathies et al. |
| 4,903,701 A | 2/1990 | Moore et al. |
| 4,909,678 A | 3/1990 | Kakimoto et al. |
| 4,913,147 A | 4/1990 | Fahlstrom et al. |
| 4,919,143 A | 4/1990 | Ayers |
| 4,924,872 A | 5/1990 | Frank |
| 4,926,903 A | 5/1990 | Kawai et al. |
| 4,932,406 A | 6/1990 | Berkovits |
| 4,934,369 A | 6/1990 | Maxwell |
| 4,936,304 A | 6/1990 | Kresh et al. |
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |

| | | |
|---|---|---|
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |

| Patent | Date | Name |
|---|---|---|
| 5,292,219 A | 3/1994 | Merin et al. |
| 5,295,967 A | 3/1994 | Rondelet et al. |
| 5,298,022 A | 3/1994 | Bernardi et al. |
| 5,298,884 A | 3/1994 | Gilmore et al. |
| 5,300,093 A | 4/1994 | Koestner et al. |
| 5,300,120 A | 4/1994 | Knapp et al. |
| 5,304,112 A | 4/1994 | Mrklas et al. |
| 5,305,923 A | 4/1994 | Kirschner et al. |
| 5,312,443 A | 5/1994 | Adams et al. |
| 5,312,452 A | 5/1994 | Salo |
| 5,312,453 A | 5/1994 | Shelton et al. |
| 5,313,953 A | 5/1994 | Yomtov et al. |
| 5,314,451 A | 5/1994 | Mulier |
| 5,314,457 A | 5/1994 | Jeutter et al. |
| 5,324,315 A | 6/1994 | Grevious |
| 5,325,834 A | 7/1994 | Ballheimer et al. |
| 5,326,249 A | 7/1994 | Weissfloch et al. |
| 5,328,460 A | 7/1994 | Lord et al. |
| 5,330,511 A | 7/1994 | Boute et al. |
| 5,337,750 A | 8/1994 | Walloch |
| 5,341,430 A | 8/1994 | Aulia et al. |
| 5,342,401 A | 8/1994 | Spano et al. |
| 5,342,406 A | 8/1994 | Thompson |
| 5,344,388 A | 9/1994 | Maxwell et al. |
| 5,347,476 A | 9/1994 | McBean, Sr. |
| 5,348,210 A | 9/1994 | Linzell et al. |
| 5,348,536 A | 9/1994 | Young et al. |
| 5,350,413 A | 9/1994 | Miller et al. |
| 5,352,180 A | 10/1994 | Candelon et al. |
| 5,353,622 A | 10/1994 | Theener |
| 5,353,800 A | 10/1994 | Pohndorf et al. |
| 5,354,200 A | 10/1994 | Klein et al. |
| 5,354,316 A | 10/1994 | Keimel |
| 5,354,319 A | 10/1994 | Wyborny et al. |
| 5,360,407 A | 11/1994 | Leonard et al. |
| 5,365,462 A | 11/1994 | McBean, Sr. |
| 5,365,619 A | 11/1994 | Solomon |
| 5,365,985 A | 11/1994 | Todd et al. |
| 5,368,040 A | 11/1994 | Carney |
| 5,370,665 A | 12/1994 | Hudrlik |
| 5,373,852 A | 12/1994 | Harrison et al. |
| 5,375,073 A | 12/1994 | McBean |
| 5,377,128 A | 12/1994 | McBean |
| 5,378,231 A | 1/1995 | Johnson et al. |
| 5,382,232 A | 1/1995 | Hague et al. |
| 5,383,915 A | 1/1995 | Adams |
| 5,388,578 A | 2/1995 | Yomtov et al. |
| 5,388,586 A | 2/1995 | Lee et al. |
| 5,388,831 A | 2/1995 | Quadri et al. |
| 5,394,909 A | 3/1995 | Mitchell et al. |
| 5,402,944 A | 4/1995 | Pape et al. |
| 5,406,957 A | 4/1995 | Tansey |
| 5,409,009 A | 4/1995 | Olson |
| 5,411,031 A | 5/1995 | Yomtov |
| 5,411,551 A | 5/1995 | Winston et al. |
| 5,411,552 A | 5/1995 | Andersen et al. |
| 5,416,372 A | 5/1995 | Ljungstroem et al. |
| 5,417,226 A | 5/1995 | Juma |
| 5,417,717 A | 5/1995 | Salo et al. |
| 5,425,362 A | 6/1995 | Siker et al. |
| 5,431,171 A | 7/1995 | Harrison et al. |
| 5,431,694 A | 7/1995 | Snaper et al. |
| 5,433,694 A | 7/1995 | Lim et al. |
| 5,437,605 A | 8/1995 | Helmy et al. |
| 5,443,215 A | 8/1995 | Fackler |
| 5,447,519 A | 9/1995 | Peterson |
| 5,449,368 A | 9/1995 | Kuzmak |
| 5,456,690 A | 10/1995 | Duong-Van |
| 5,461,390 A | 10/1995 | Hoshen |
| 5,464,435 A | 11/1995 | Neumann |
| 5,467,627 A | 11/1995 | Smith et al. |
| 5,474,226 A | 12/1995 | Joseph |
| 5,479,818 A | 1/1996 | Walter et al. |
| 5,482,049 A | 1/1996 | Addiss et al. |
| 5,487,760 A | 1/1996 | Villafana |
| 5,493,738 A | 2/1996 | Sanderson et al. |
| 5,494,036 A | 2/1996 | Uber, III et al. |
| 5,494,193 A | 2/1996 | Kirschner et al. |
| 5,504,474 A | 4/1996 | Libman et al. |
| 5,505,916 A | 4/1996 | Berry, Jr. |
| 5,507,412 A | 4/1996 | Ebert et al. |
| 5,507,737 A | 4/1996 | Palmskog et al. |
| 5,507,785 A | 4/1996 | Deno |
| 5,509,888 A | 4/1996 | Miller |
| 5,509,891 A | 4/1996 | DeRidder |
| 5,513,945 A | 5/1996 | Hartmann et al. |
| 5,514,103 A | 5/1996 | Srisathapat et al. |
| 5,518,504 A | 5/1996 | Polyak |
| 5,520,606 A | 5/1996 | Schoolman et al. |
| 5,523,740 A | 6/1996 | Burgmann et al. |
| 5,534,018 A | 7/1996 | Wahlstrand et al. |
| 5,535,752 A | 7/1996 | Halperin et al. |
| 5,538,005 A | 7/1996 | Harrison et al. |
| 5,541,857 A | 7/1996 | Walter et al. |
| 5,545,140 A | 8/1996 | Conero et al. |
| 5,545,151 A | 8/1996 | O'Connor et al. |
| 5,545,186 A | 8/1996 | Olson et al. |
| 5,545,214 A | 8/1996 | Stevens |
| 5,547,470 A | 8/1996 | Johnson et al. |
| 5,551,427 A | 9/1996 | Altman |
| 5,551,439 A | 9/1996 | Hickey |
| 5,554,185 A | 9/1996 | Block et al. |
| 5,558,644 A | 9/1996 | Boyd et al. |
| 5,564,434 A | 10/1996 | Halperin et al. |
| 5,575,770 A | 11/1996 | Melsky et al. |
| 5,584,803 A | 12/1996 | Stevens et al. |
| 5,586,629 A | 12/1996 | Shoberg et al. |
| 5,593,430 A | 1/1997 | Renger |
| 5,594,665 A | 1/1997 | Walter et al. |
| 5,596,986 A | 1/1997 | Goldfarb |
| 5,597,284 A | 1/1997 | Weltlich et al. |
| 5,610,083 A | 3/1997 | Chan et al. |
| 5,611,768 A | 3/1997 | Tutrone, Jr. |
| 5,612,497 A | 3/1997 | Walter et al. |
| 5,615,671 A | 4/1997 | Schoonen et al. |
| 5,619,991 A | 4/1997 | Sloane |
| 5,625,946 A | 5/1997 | Wildeson et al. |
| 5,626,623 A | 5/1997 | Kieval et al. |
| 5,626,630 A | 5/1997 | Markowitz et al. |
| 5,630,836 A | 5/1997 | Prem et al. |
| 5,634,255 A | 6/1997 | Bishop et al. |
| 5,637,083 A | 6/1997 | Bertrand et al. |
| 5,643,207 A | 7/1997 | Rise |
| 5,645,116 A | 7/1997 | McDonald |
| 5,650,766 A | 7/1997 | Burgmann et al. |
| 5,673,585 A | 10/1997 | Bishop et al. |
| 5,676,690 A | 10/1997 | Noren et al. |
| 5,681,285 A | 10/1997 | Ford et al. |
| 5,686,831 A | 11/1997 | Vandervalk et al. |
| 5,687,734 A | 11/1997 | Dempsey et al. |
| 5,693,076 A | 12/1997 | Kaemmerer |
| 5,702,368 A | 12/1997 | Stevens et al. |
| 5,702,427 A | 12/1997 | Ecker et al. |
| 5,702,431 A | 12/1997 | Wang et al. |
| 5,704,352 A | 1/1998 | Tremblay et al. |
| 5,715,786 A | 2/1998 | Seiberth et al. |
| 5,715,837 A | 2/1998 | Chen |
| 5,720,436 A | 2/1998 | Buschor et al. |
| 5,730,101 A | 3/1998 | Aupperle et al. |
| 5,732,710 A | 3/1998 | Rabinovich et al. |
| 5,733,313 A | 3/1998 | Barreras, Sr. et al. |
| 5,738,652 A | 4/1998 | Boyd et al. |
| 5,742,233 A | 4/1998 | Hoffman et al. |
| 5,743,267 A | 4/1998 | Nikolic et al. |
| 5,749,369 A | 5/1998 | Rabinovich et al. |
| 5,749,909 A | 5/1998 | Schroeppel et al. |
| 5,755,687 A | 5/1998 | Donlon |
| 5,755,748 A | 5/1998 | Borza et al. |
| 5,765,568 A | 6/1998 | Sweezer, Jr. et al. |
| 5,769,812 A | 6/1998 | Stevens et al. |
| 5,771,903 A | 6/1998 | Jakobsson |
| 5,782,774 A | 7/1998 | Shmulewitz |
| 5,787,520 A | 8/1998 | Dunbar |
| 5,791,344 A | 8/1998 | Schulman et al. |
| 5,792,094 A | 8/1998 | Stevens et al. |
| 5,792,179 A | 8/1998 | Sideris |
| 5,795,325 A | 8/1998 | Valley et al. |
| 5,796,827 A | 8/1998 | Coppersmith et al. |

| | | |
|---|---|---|
| 5,800,375 A | 9/1998 | Sweezer et al. |
| 5,807,265 A | 9/1998 | Itoigawa et al. |
| 5,807,336 A | 9/1998 | Russo et al. |
| 5,810,015 A | 9/1998 | Flaherty |
| 5,810,757 A | 9/1998 | Sweezer, Jr. et al. |
| 5,814,016 A | 9/1998 | Valley et al. |
| 5,817,093 A | 10/1998 | Williamson, IV et al. |
| 5,833,603 A | 11/1998 | Kovacs et al. |
| 5,836,300 A | 11/1998 | Mault |
| 5,836,886 A | 11/1998 | Itoigawa et al. |
| 5,840,081 A | 11/1998 | Andersen et al. |
| 5,849,225 A | 12/1998 | Ebina et al. |
| 5,855,597 A | 1/1999 | Jayaraman et al. |
| 5,855,601 A | 1/1999 | Bessler et al. |
| 5,860,938 A | 1/1999 | Lafontaine et al. |
| 5,861,018 A | 1/1999 | Feierbach |
| 5,863,366 A | 1/1999 | Snow |
| 5,868,702 A | 2/1999 | Stevens et al. |
| 5,873,837 A | 2/1999 | Lieber et al. |
| 5,875,953 A | 3/1999 | Shioya et al. |
| 5,879,499 A | 3/1999 | Corvi |
| 5,881,919 A | 3/1999 | Womac et al. |
| 5,885,238 A | 3/1999 | Stevens et al. |
| 5,887,475 A | 3/1999 | Muldner |
| 5,899,927 A | 5/1999 | Ecker et al. |
| 5,916,179 A | 6/1999 | Sharrock |
| 5,916,237 A | 6/1999 | Schu |
| 5,935,078 A | 8/1999 | Feierbach |
| 5,938,669 A | 8/1999 | Klaiber et al. |
| 5,951,487 A | 9/1999 | Brehmeier-Flick et al. |
| 5,957,861 A | 9/1999 | Combs et al. |
| 5,967,986 A | 10/1999 | Cimochowski et al. |
| 5,971,934 A | 10/1999 | Scherer et al. |
| 5,974,873 A | 11/1999 | Nelson et al. |
| 5,978,985 A | 11/1999 | Thurman |
| 5,995,874 A | 11/1999 | Borza et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,030,413 A | 2/2000 | Lazarus |
| 6,035,461 A | 3/2000 | Nguyen |
| 6,053,873 A | 4/2000 | Govari et al. |
| 6,056,723 A | 5/2000 | Donlon |
| 6,058,330 A | 5/2000 | Borza et al. |
| 6,059,757 A | 5/2000 | Macoviak et al. |
| 6,067,474 A | 5/2000 | Schulman et al. |
| 6,067,991 A | 5/2000 | Forsell et al. |
| 6,076,016 A | 6/2000 | Feierbach |
| 6,083,174 A | 7/2000 | Brehmeier-Flick et al. |
| 6,090,096 A | 7/2000 | St. Goar et al. |
| 6,102,678 A | 8/2000 | Peclat et al. |
| 6,102,856 A | 8/2000 | Groff et al. |
| 6,102,922 A | 8/2000 | Jakobsson et al. |
| 6,106,477 A | 8/2000 | Miesel et al. |
| 6,106,551 A | 8/2000 | Crossett et al. |
| 6,110,145 A | 8/2000 | Macoviak |
| 6,113,553 A | 9/2000 | Chubbuck |
| 6,131,664 A | 10/2000 | Sonnier |
| 6,135,945 A | 10/2000 | Sultan |
| 6,159,156 A | 12/2000 | Van Bockel et al. |
| 6,162,180 A | 12/2000 | Miesel et al. |
| 6,162,245 A | 12/2000 | Jayaraman et al. |
| 6,168,614 B1 | 1/2001 | Andersen et al. |
| 6,234,745 B1 | 5/2001 | Pugh et al. |
| 6,240,316 B1 | 5/2001 | Richmond et al. |
| 6,240,318 B1 | 5/2001 | Phillips |
| 6,245,102 B1 | 6/2001 | Jayaraman |
| 6,248,080 B1 | 6/2001 | Miesel et al. |
| 6,251,093 B1 | 6/2001 | Valley et al. |
| 6,269,819 B1 | 8/2001 | Oz et al. |
| 6,277,078 B1 | 8/2001 | Porat et al. |
| 6,292,697 B1 | 9/2001 | Roberts |
| 6,309,350 B1 | 10/2001 | VanTassel et al. |
| 6,315,769 B1 | 11/2001 | Peer et al. |
| 6,319,208 B1 | 11/2001 | Abita et al. |
| 6,328,699 B1 | 12/2001 | Eigler et al. |
| 6,338,735 B1 | 1/2002 | Stevens |
| 6,357,438 B1 | 3/2002 | Hansen |
| 6,360,122 B1 | 3/2002 | Fischell et al. |
| 6,360,822 B1 | 3/2002 | Robertson et al. |
| 6,366,817 B1 | 4/2002 | Kung |
| 6,379,308 B1 | 4/2002 | Brockway et al. |
| 6,379,380 B1 | 4/2002 | Satz |
| 6,398,752 B1 | 6/2002 | Sweezer, Jr. et al. |
| 6,409,674 B1 | 6/2002 | Brockway et al. |
| 6,423,031 B1 | 7/2002 | Donlon |
| 6,430,444 B1 | 8/2002 | Borza et al. |
| 6,431,175 B1 | 8/2002 | Penner et al. |
| 6,432,040 B1 | 8/2002 | Meah |
| 6,443,887 B1 | 9/2002 | Derus et al. |
| 6,443,893 B1 | 9/2002 | Schnakenberg et al. |
| 6,450,173 B1 | 9/2002 | Forsell et al. |
| 6,450,946 B1 | 9/2002 | Forsell et al. |
| 6,453,907 B1 | 9/2002 | Forsell et al. |
| 6,454,698 B1 | 9/2002 | Forsell et al. |
| 6,454,699 B1 | 9/2002 | Forsell et al. |
| 6,454,700 B1 | 9/2002 | Forsell et al. |
| 6,454,701 B1 | 9/2002 | Forsell et al. |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell et al. |
| 6,464,628 B1 | 10/2002 | Forsell et al. |
| 6,470,212 B1 | 10/2002 | Weijand et al. |
| 6,470,892 B1 | 10/2002 | Forsell et al. |
| 6,471,635 B1 | 10/2002 | Forsell et al. |
| 6,475,136 B1 | 11/2002 | Forsell et al. |
| 6,475,170 B1 | 11/2002 | Doron et al. |
| 6,482,145 B1 | 11/2002 | Forsell et al. |
| 6,482,171 B1 | 11/2002 | Corvi et al. |
| 6,482,177 B1 | 11/2002 | Leinders et al. |
| 6,486,588 B2 | 11/2002 | Doron et al. |
| 6,503,189 B1 | 1/2003 | Forsell et al. |
| 6,504,286 B1 | 1/2003 | Porat et al. |
| 6,531,739 B2 | 3/2003 | Cable et al. |
| 6,533,719 B2 | 3/2003 | Kuyava et al. |
| 6,533,733 B1 | 3/2003 | Hylton et al. |
| 6,542,350 B1 | 4/2003 | Rogers |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | Van Tassel et al. |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Pease et al. |
| 6,736,846 B2 | 5/2004 | Cox |
| 6,752,813 B2 | 6/2004 | Goldfarb et al. |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |

| | | |
|---|---|---|
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 7,558,629 B2 | 7/2009 | Keimel et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2004/0054352 A1 | 3/2004 | Adams et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0061079 A1 | 3/2005 | Schulman |
| 2005/0090873 A1 | 4/2005 | Imran |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0173238 A1 | 8/2006 | Starkebaum |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247721 A1 | 11/2006 | Machino |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0161958 A1 | 7/2007 | Glenn |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2008/0009680 A1 | 1/2008 | Hassler |

FOREIGN PATENT DOCUMENTS

| | | |
|---|---|---|
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1059035 | 2/1992 |
| CN | 1119469 | 3/1996 |
| CN | 1241003 | 1/2000 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 0941712 A1 | 9/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| EP | 1815881 A1 | 8/2007 |
| EP | 1832252 A2 | 9/2007 |
| FR | 2730158 A1 | 8/1996 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0009047 A1 | 2/2000 |
| WO | WO-0033738 | 6/2000 |
| WO | WO-0072899 | 12/2000 |
| WO | WO-014487 | 1/2001 |
| WO | WO-0108597 A1 | 2/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014245 A1 | 2/2004 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2004112563 A2 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006108203 A2 | 10/2006 |
| WO | WO-2006113187 | 10/2006 |
| WO | WO-2006118790 A2 | 11/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |
| WO | WO-2008117296 A1 | 10/2008 |

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C278B-9EBF-AAC8-9FAF8851256D&sel=1&sel4=1;1 page, Sep. 10, 2008.

"Radiation Hardened Electronics and Radiation Technology", Honeywell product and service information from website http://www.honeywell.com/sites/portal?smap=aerospace&page=Radiation-Hardened-Electronics&theme=T4; 2 pages, Oct. 13, 2007.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

METHODS AND DEVICES FOR MEASURING IMPEDANCE IN A GASTRIC RESTRICTION SYSTEM

FIELD OF THE INVENTION

The present invention relates to devices and methods for gathering impedance data related to implantable restriction devices.

BACKGROUND OF THE INVENTION

Obesity is becoming a growing concern, particularly in the United States, as the number of obese people continues to increase and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a Huber needle and syringe were used to penetrate the patient's skin and add or remove fluid from the balloon via an injection port. More recently, implantable pumps have been developed which enable non-invasive adjustments of the band. An external programmer communicates with the implanted pump using telemetry to control the pump. During a scheduled visit, a physician places a handheld portion of the programmer near the gastric implant and transmits power and command signals to the implant. The implant in turn adjusts the fluid levels in the band and transmits a response command to the programmer.

During these gastric band adjustments, it has been difficult to determine how the adjustment is proceeding and whether the adjustment will have the intended effect. In an attempt to determine the efficacy of an adjustment, some physicians have utilized fluoroscopy with a Barium swallow as the adjustment is being performed. However, fluoroscopy is both expensive and undesirable due to the radiation doses incurred by both the physician and patient. Other physicians have instructed the patient to drink a glass of water during or after the adjustment to determine whether the water can pass through the adjusted stoma. This method, however, only assures that the patient is not obstructing and does not provide any information about the efficacy of the adjustment. Oftentimes, a physician may simply adopt a "try as you go" method based upon their prior experience, and the results of an adjustment may not be discovered until hours or days later, when the patient experiences a complete obstruction to the stomach cavity, or the band induces erosion of the stomach tissue due excessive interface pressures against the band.

Accordingly, methods and devices are provided for use with an implantable restriction device, and in particular for gathering impedance data related to an implantable restriction device.

SUMMARY OF THE INVENTION

The present invention generally provides methods and devices for gathering impedance data related to implantable restriction devices. In one embodiment, a restriction system for forming a restriction in a patient is provided that includes an implantable restriction device, (e.g., an adjustable gastric band) configured to form a restriction in a patient. The system also includes at least two sensor electrodes disposed on a tissue-contacting surface of the implantable restriction device and an impedance measuring device that can be in electronic communication with the sensor electrodes and measure an impedance between the sensor electrodes. In some embodiments, the sensor electrodes can be in contact with tissue proximate to the restriction formed by the implantable restriction device, and the impedance measuring device can measure the impedance of the tissue.

The system can also include a processor that can compare an impedance measured between the sensor electrodes with a range of impedance values. In some embodiments, the system includes a processor that can signal for a corrective action (e.g., suggesting a change in pressure within the implantable restriction device and/or a modification of the patient's treatment plan) if the impedance measuring device measures an impedance between the sensor electrodes that differs from a threshold impedance value and/or a range of impedance values. The threshold impedance value can reflect a baseline amount of tissue proximate to the restriction formed by the implantable restriction device. A measured impedance value that differs from the threshold impedance value can indicate either patient weight loss or patient weight gain. The processor can also, in some embodiments, determine if measured impedance values gathered over a period of time are each at a substantially constant value indicative of a weight loss plateau, and, if so, to signal an alarm.

In another embodiment, a restriction system for forming a restriction in a patient includes an implantable measuring device that can be in communication with an implantable restriction device that can form a restriction in a patient. The implantable measuring device can also gather data related to a weight of the patient. The system also includes a controller that can signal for an adjustment of the patient's treatment concerning the implantable restriction device if the gathered data indicates an inflection regarding the weight of the patient, e.g., an inflection in a plot line indicating a minimization of a fat pad of the patient. The signal for an adjustment of the patient's treatment can include, for example, a signal to adjust an amount of fluid within the implantable restriction device and/or to modify the patient's treatment plan. In some embodiments, the system also includes a pressure sensor that can sense a pressure of fluid within the implantable restriction device and communicate pressure data to the controller. The controller can use the pressure data to corroborate an inflection regarding the weight of the patient and signal for an adjustment of the patient's treatment if so corroborated. In some embodiments, the measuring device includes at least two sensor electrodes disposed on a tissue-contacting surface on the implantable restriction device and an impedance measuring device that can be in electronic communication with the sensor electrodes and measure an impedance between the sensor electrodes. The sensor electrodes can be in contact with tissue proximate to the restriction formed by the implantable restriction device, and the impedance measuring device can measure the impedance of the tissue. The controller can signal for a change of fluid volume within the implantable restriction device if the measured impedance falls within a range of impedance values.

In other aspects, a method of controlling weight loss in a patient is provided. The method includes providing a restriction device that can be implantable in a patient and have at least two electrodes on a tissue-contacting surface thereof. The method also includes measuring with an impedance sensor an impedance of tissue surrounded by the restriction device. In some embodiments, the method also includes coupling the impedance sensor to a tissue-contacting surface of the restriction device. A difference between the measured impedance of the tissue and an immediately prior measured impedance of the tissue can indicate at least one of a bolus of food and a fold in the tissue between the two electrodes. In some embodiments, the method also includes triggering an alarm signal if the measured impedance differs from a threshold impedance value, falls outside a range of impedance values, or if measured impedance values gathered over a period of time are each at a substantially constant value indicative of a weight loss plateau. Triggering an alarm signal can include transmitting a signal to an external display device that can display a notice indicating that the measured impedance differs from the threshold impedance value, falls outside a range of impedance values, or indicates a weight loss plateau. Additionally or alternatively, if an alarm signal is triggered, the method can include adjusting an amount of fluid within the restriction device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for gathering impedance data related to implantable restriction devices. In general, the devices and methods can enable patients, health care providers, and others to use gathered data as a feedback mechanism to non-invasively monitor efficacy of an implantable restriction device in a patient and to identify, modify, and/or prescribe a treatment plan for the patient considering the gathered data. Such data can also be used in counseling and motivating the patient regarding weight loss progress by, for example, identifying a weight loss inflection. Impedance data can be gathered and analyzed for tissue proximate to the restriction device, e.g., a fat pad between a gastric band and the patient's stomach. Because tissue is conductive, and because material (e.g., silicone) used for the restriction device is typically not, current can travel along the tissue. Electrodes in contact with the tissue can therefore measure an impedance of the tissue, with the impedance between the electrodes changing as the tissue reduces in size (e.g., because impedance decreases as fat cells shrink) and/or changes configuration. Moreover, because such impedance data can indicate tissue size, with the impedance asymptotically converging on a final value indicating a minimized tissue size, the impedance data can be used in future analysis, such as in correlating fat pad size with weight loss profiles, speed of weight loss, and/or other factors.

Figure 1A:
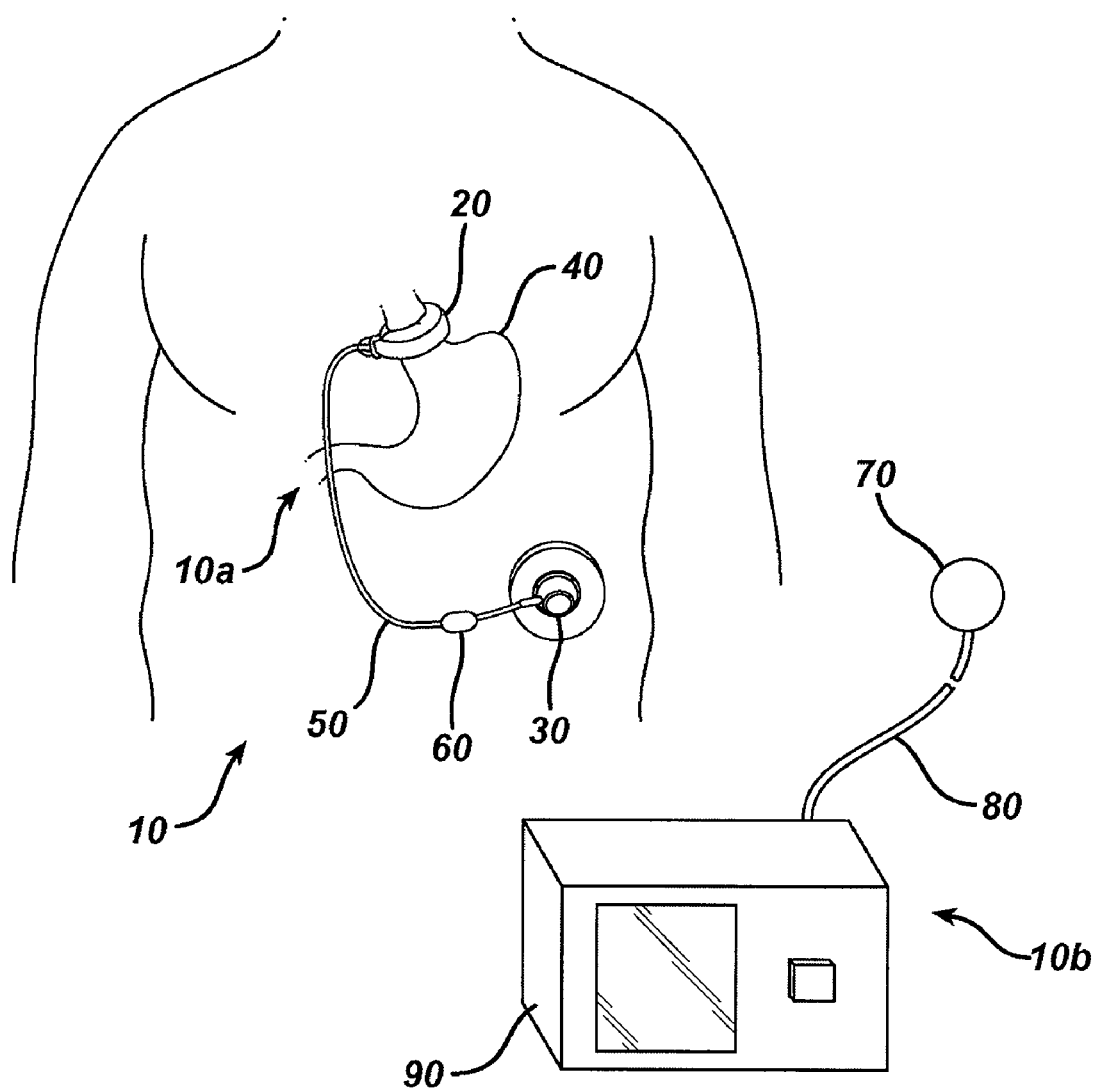
FIG. 1A is a schematic diagram of an embodiment of a food intake restriction system.
Figure 1B:
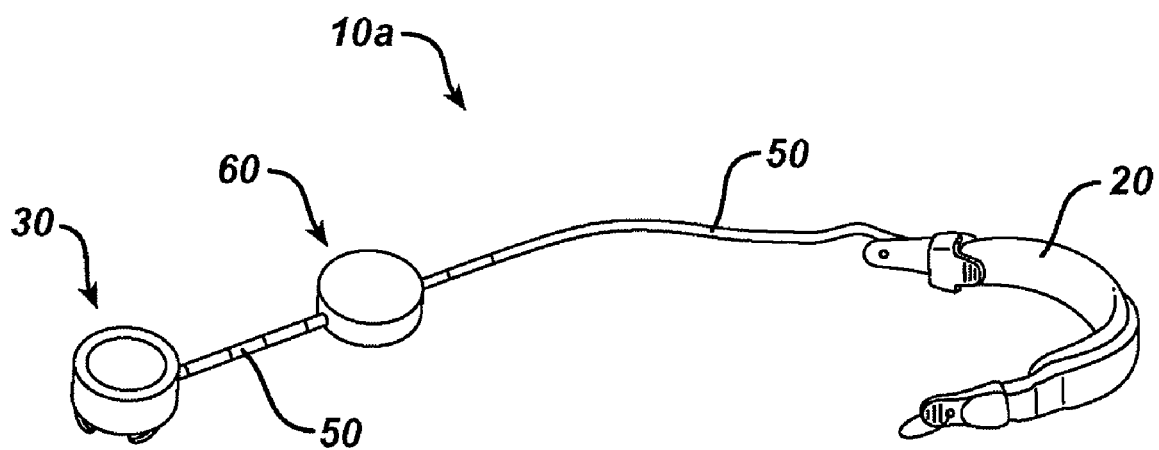
FIG. 1B is a perspective view of an embodiment of an implantable portion of the food intake restriction system of FIG. 1A.

While the present invention can be used with a variety of restriction systems known in the art, FIG. 1A illustrates one exemplary embodiment of a food intake restriction system 10 in use in a patient. As shown, the system 10 generally includes an implantable portion 10a and an external portion 10b. FIG. 1B illustrates the implantable portion 10a outside of a patient. As shown, the implantable portion 10a includes an adjustable gastric band 20 that is configured to be positioned around the upper portion of a patient's stomach 40, and an injection port housing 30 that is fluidly coupled to the adjustable gastric band 20, e.g., via a catheter 50. The injection port 30 is adapted to allow fluid to be introduced into and removed from the gastric band 20 to thereby adjust the size of the band 20 and thus the pressure applied to the stomach 40. The injection port 30 can thus be implanted at a location within the body that is accessible through tissue. Typically, injection ports are positioned in the lateral subcostal region of the patient's abdomen under the skin and layers of fatty tissue. Surgeons also typically implant injection ports on the sternum of the patient.

A sensing or measuring device can be implanted in the patient to contact tissue surrounding or partially surrounding one or more elements included in the implantable portion 10a. In one embodiment, the measuring device is an impedance measuring device configured to be in contact with tissue and measure an impedance of the tissue. While the impedance sensing device can have various configurations and be positioned anywhere within the patient, including within the injection port 30, in the illustrated embodiment the impedance sensing device is in the form of an impedance measuring device within a sensor housing 60 and in electrical communication (wired or wireless) with one or more sensor electrodes. The sensor electrodes can also have various configurations, be of any number, and be disposed in contact with any tissue (e.g., fat tissue, an organ, etc.), but in this embodiment, two impedance sensing electrodes are disposed on a tissue-contacting surface (e.g., an external surface) of the band 20. The sensing electrodes can rest on a tissue's surface and/or penetrate into tissue. A circumferential array of sensor electrodes can provide a higher resolution by increasing the number of the discrete measurement points, thereby increasing the accuracy and precision of the cumulative measured impedances in the surrounding tissue.

A sensing or measuring device that is in fluid communication with the closed fluid circuit can also be included in the implantable portion 10a. In one embodiment, the sensing device is a pressure sensing device configured to measure the fluid pressure of the closed fluid circuit. While the pressure measuring device can have various configurations and be positioned anywhere along the internal portion 10a, including within the injection port 30, in the illustrated embodiment the pressure measuring device is in the form of a pressure sensor that is disposed within the sensor housing 60 positioned adjacent to the injection port 30. The catheter 50 can include a first portion that is coupled between the gastric band 20 and the sensor housing 60, and a second portion that is coupled between the sensor housing 60 and the injection port 30.

In addition to sensing pressure of fluid within the internal portion 10a as described herein, pressure of fluid within the esophagus and/or the stomach 40 can also be sensed using any suitable device, such as an endoscopic manometer. By way of non-limiting example, such fluid pressure measurements can be compared against measured pressure of fluid within the internal portion 10a before, during, and/or after adjustment of pressure within the internal portion 10a. Other suitable uses for measured pressure within the esophagus and/or the stomach 40 will be appreciated by those skilled in the art.

While it is understood that a sensing device can be configured to obtain data relating to one or more relevant parameters, generally, sensing devices will be described herein in the context of an impedance sensing device and a pressure sensing device.

As further shown in FIG. 1A, the external portion 10b generally includes a data reading device 70 that is configured to be positioned on the skin surface above an implanted element (e.g., the band 20, the sensor housing 60, the port housing 30, etc.), which can be implanted beneath thick tissue (e.g., over 10 cm thick), to non-invasively communicate with the element and thereby obtain data. The reading device 70 can optionally be electrically coupled (wirelessly or wired, as in this embodiment via an electrical cable assembly 80) to a control box 90 that can display data such as pressure measurements, impedance measurements, and/or other data obtained from the data reading device 70. While shown in this example as located local to the patient, the control box 90 can be at a location local to or remote from the patient, as explained further below.

Figure 2A:
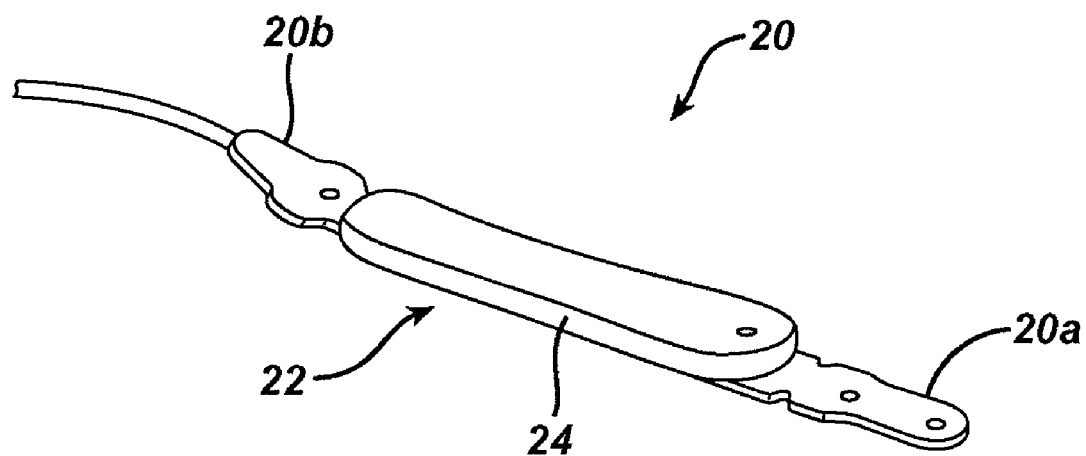
FIG. 2A is a perspective view of the food intake restriction device of FIG. 1A.

FIG. 2A shows the gastric band 20 in more detail. While the gastric band 20 can have a variety of configurations, and various gastric bands currently known in the art can be used with the present invention, in the illustrated embodiment the gastric band 20 has a generally elongate shape with a support structure 22 having first and second opposite ends 20a, 20b that can be formed in a loop such that the ends are secured to each other. Various mating techniques can be used to secure the ends 20a, 20b to one another. In the illustrated embodiment, the ends 20a, 20b are in the form of straps that mate together, with one laying on top of the other. In another embodiment, illustrated, for example, in FIGS. 1B and 2B, a support structure at one end of the gastric band 20 can include an opening through which the other end of the gastric band 20 can feed through to secure the ends to one another. The gastric band 20 can also include a variable volume member, such as an inflatable balloon 24, that is disposed or formed on one side of the support structure 22 and that is configured to be positioned adjacent to tissue. The balloon 24 can expand or contract against the outer wall of the stomach to form an adjustable stoma for controllably restricting food intake into the stomach.

A person skilled in the art will appreciate that the gastric band can have a variety of other configurations. Moreover, the various methods and devices disclosed herein have equal applicability to other types of implantable bands. For example, bands are used for the treatment of fecal incontinence, as described in U.S. Pat. No. 6,461,292 which is hereby incorporated by reference. Bands can also be used to treat urinary incontinence, as described in U.S. Publication No. 2003/0105385 which is hereby incorporated by reference. Bands can also be used to treat heartburn and/or acid reflux, as disclosed in U.S. Pat. No. 6,470,892 which is hereby incorporated by reference. Bands can also be used to treat impotence, as described in U.S. Publication No. 2003/0114729 which is hereby incorporated by reference.

Figure 2B:
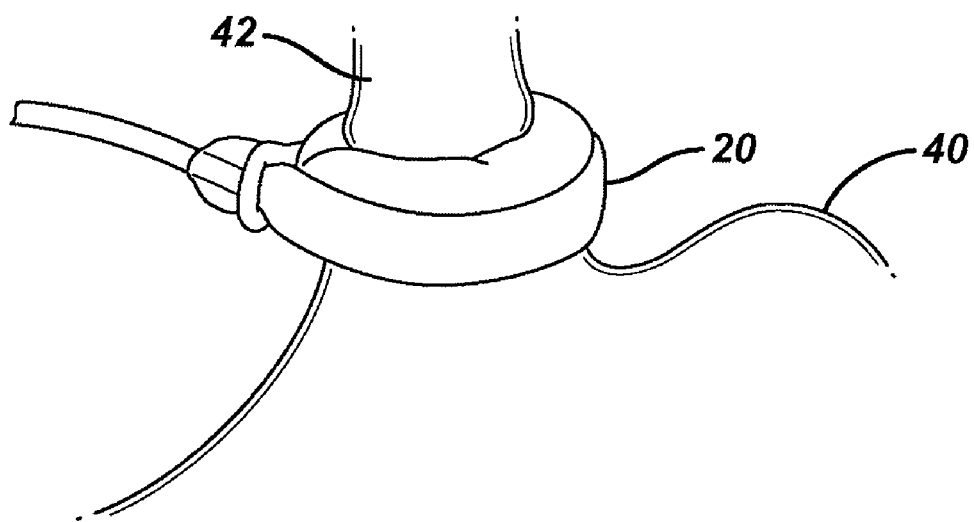
FIG. 2B is a schematic diagram of the food intake restriction device of FIG. 2A applied about the gastro-esophageal junction of a patient.

FIG. 2B shows the adjustable gastric band 20 applied about the gastro-esophageal junction of a patient. As shown, the band 20 at least substantially encloses the upper portion of the stomach 40 near the junction with the patient's esophagus 42. After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band 20.

Figure 3:
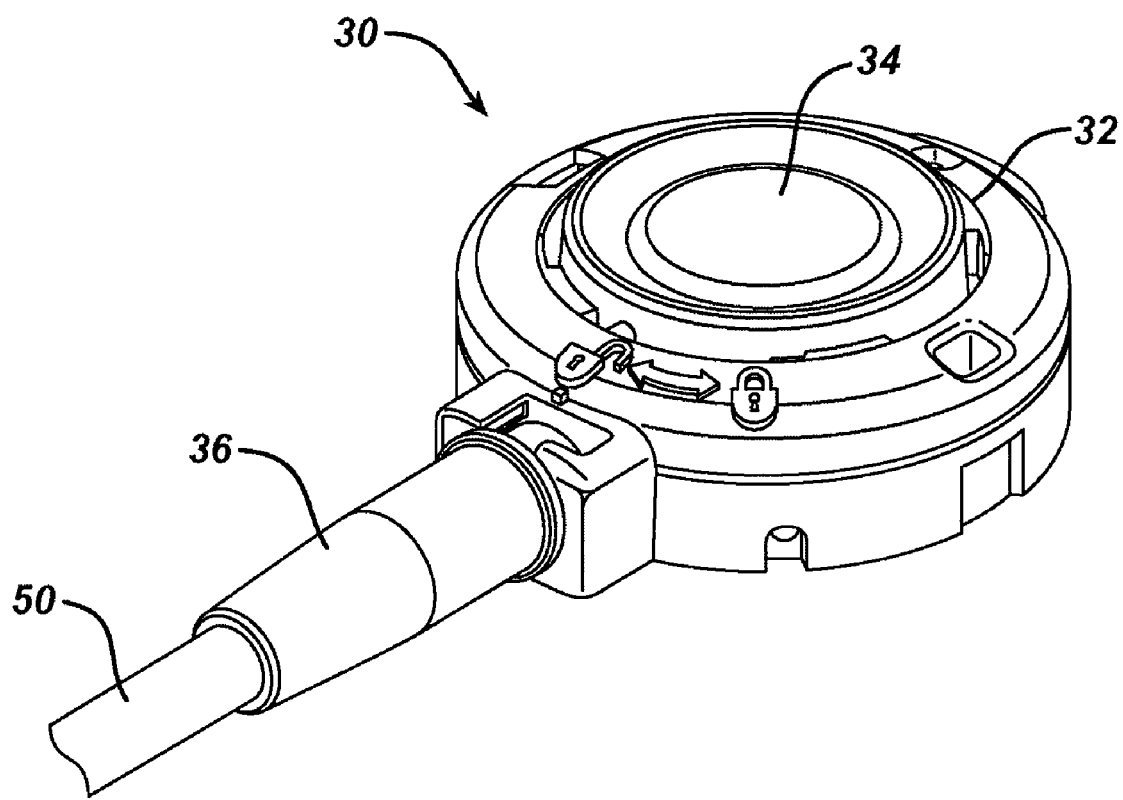
FIG. 3 is a perspective view of an embodiment of the injection port housing of FIG. 1A.

The fluid injection port 30 can also have a variety of configurations. In the embodiment shown in FIG. 3, the injection port 30 has a generally cylindrical housing with a distal or bottom surface and a perimeter wall extending proximally from the bottom surface and defining a proximal opening 32. The proximal opening 32 can include a needle-penetrable septum 34 extending there across and providing access to a fluid reservoir (not visible in FIG. 3) formed within the housing. The septum 34 is preferably placed in a proximal enough position such that the depth of the reservoir is sufficient enough to expose the open tip of a needle, such as a Huber needle, so that fluid transfer can take place. The septum 34 is preferably arranged so that it will self seal after being punctured by a needle and the needle is withdrawn. As further shown in FIG. 3, the port 30 can further include a catheter tube connection member 36 that is in fluid communication with the reservoir and that is configured to couple to a catheter (e.g., the catheter 50). A person skilled in the art will appreciate that the housing can be made from any number of materials, including stainless steel, titanium, or polymeric materials, and the septum 34 can likewise be made from any number of materials, including silicone.

The reading device 70 can also have a variety of configurations, and one exemplary pressure reading device is disclosed in more detail in commonly-owned U.S. Publication No. 2006/0189888 and U.S. Publication No. 2006/0199997, which are hereby incorporated by reference. In general, the reading device 70 can non-invasively measure the pressure of the fluid within the implanted portion 10a even when the pressure sensing device is implanted beneath thick (at least over 10 cm) subcutaneous fat tissue. The physician can hold the reading device 70 against the patient's skin near the location of the sensor housing 60, other pressure sensing device location(s), and/or location(s) of other data-gathering devices, such as the impedance system described further below, and observe the pressure reading on a display on the control box 90. The reading device 70 can also be removably attached to the patient, as discussed further below, such as during a prolonged examination, using straps, adhesives, and other well-known methods. The reading device 70 can operate through conventional cloth or paper surgical drapes, and can also include a disposal cover (not shown) that may be replaced for each patient.

Figure 4:
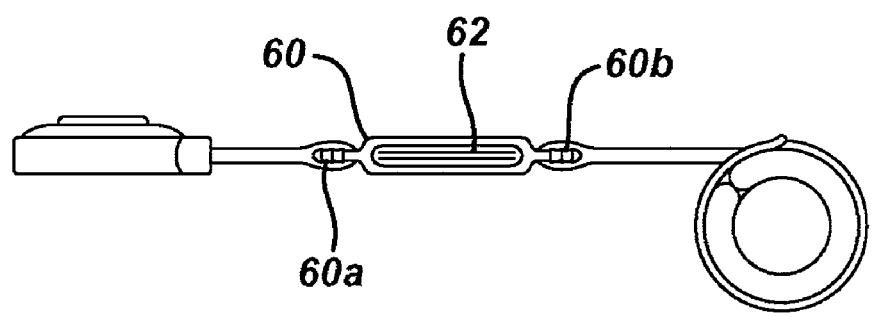
FIG. 4 is a perspective view of an embodiment of the sensor housing of FIG. 1A.

As indicated above, the system 10 can also include a pressure measuring device in communication with the closed fluid circuit and configured to measure pressure (e.g., fluid pressure) which corresponds to the amount of restriction applied by the adjustable gastric band 20 to the patient's stomach 40. Measuring the pressure can enables an evaluation of the efficacy and functionality of the restriction created by a band adjustment. In the illustrated embodiment, as shown in FIG. 4, the pressure measuring device is in the form of a pressure sensor 62 disposed within the sensor housing 60. The pressure measuring device can, however, be disposed anywhere within the closed hydraulic circuit of the implantable portion, and various exemplary locations and configurations are disclosed in more detail in commonly-owned U.S. Publication No. 2006/0211913 entitled "Non-Invasive Pressure Measurement In a Fluid Adjustable Restrictive Device," filed on Mar. 7, 2006, and hereby incorporated by reference.

In general, the illustrated sensor housing 60 includes an inlet 60a and an outlet 60b that are in fluid communication with the fluid in the implantable portion 10a. An already-implanted catheter 50 can be retrofitted with the sensor housing 60, such as by severing the catheter 50 and inserting barbed connectors (or any other connectors, such as clamps, clips, adhesives, welding, etc.) into the severed ends of the catheter 50. The sensor 62 can be disposed within the housing 60 and be configured to respond to fluid pressure changes within the hydraulic circuit and convert the pressure changes into a usable form of data. As further discussed below, the pressure sensing system can also include a microcontroller (e.g., a processor), a TET/telemetry coil, and a capacitor. Optionally, the pressure sensing system can further comprise a temperature sensor. The microcontroller, the TET/telemetry coil, and the capacitor can be in communication via a circuit board or any via any other suitable component(s). It will also be appreciated that the TET/telemetry coil and the capacitor can collectively form a tuned tank circuit for receiving power from the external portion 10b and transmitting data to the reading device 70. Moreover, to the extent that a telemetry component is unable to reach a telemetry device external to the patient without some assistance, such assistance can be provided by any suitable number of relays (not shown) or other devices.

Various pressure sensors known in the art can be used as the pressure sensor 62, such as a wireless pressure sensor provided by CardioMEMS, Inc. of Atlanta, Ga., though a suitable MEMS pressure sensor may be obtained from any other source, including but not limited to Integrated Sensing Systems, Inc. (ISSYS) of Ypsilanti, Mich. and Remon Medical Technologies, Inc. of Waltham, Mass. One exemplary MEMS pressure sensor is described in U.S. Pat. No. 6,855,115, the disclosure of which is incorporated by reference herein for illustrative purposes only. It will also be appreciated by a person skilled in the art that suitable pressure sensors can include, but are not limited to, capacitive, piezoresistive, silicon strain gauge, or ultrasonic (acoustic) pressure sensors, as well as various other devices capable of measuring pressure.

Figure 5:
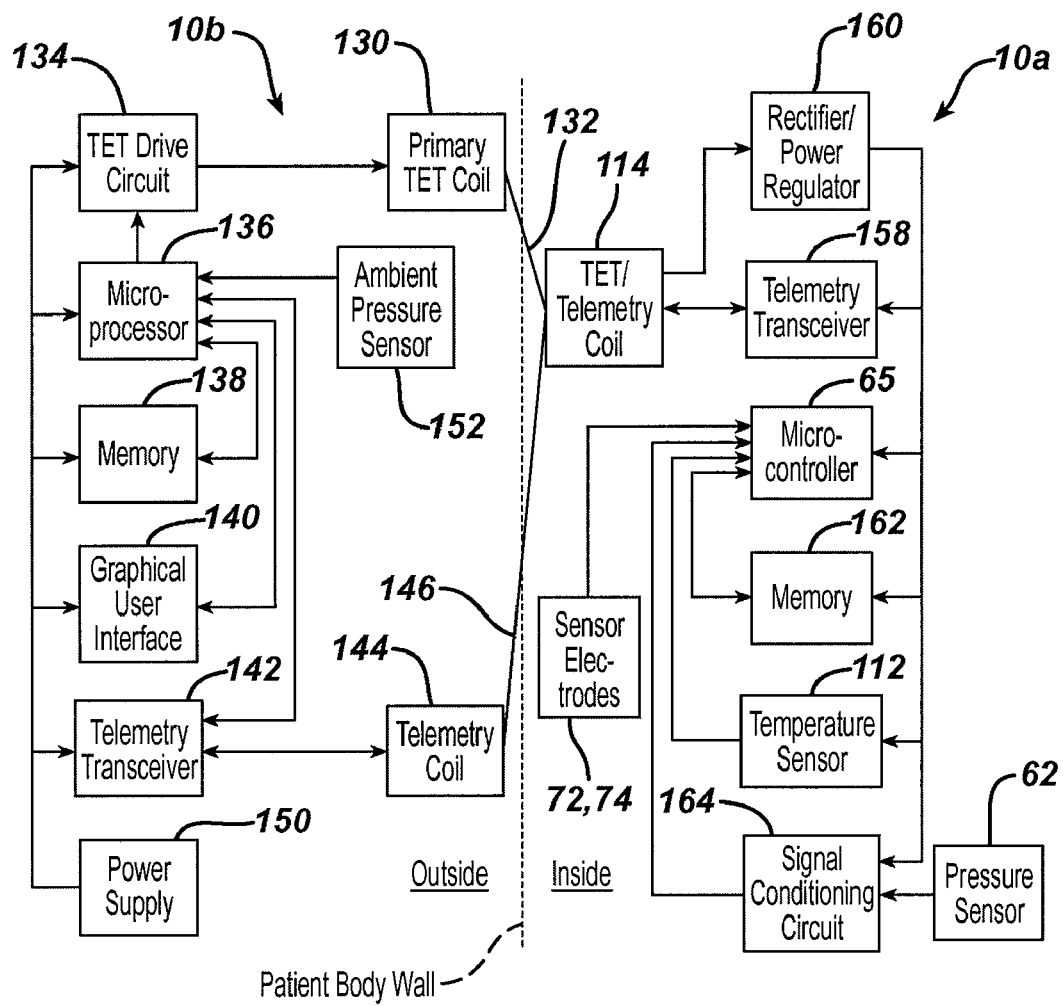
FIG. 5 is a block diagram showing an embodiment of internal and external components of the food intake restriction device of FIG. 1A.

FIG. 5 illustrates one embodiment of components included in the internal and external portions 10a, 10b of the food intake restriction system 10. As shown in FIG. 5, the external portion 10b includes a primary TET coil 130 for transmitting a power signal 132 to the internal portion 10a. A telemetry coil 144 is also included for transmitting data signals to the internal portion 10a. The primary TET coil 130 and the telemetry coil 144 combine to form an antenna, e.g., the reading device 70. The external portion 10b, e.g., disposed in the control box 90, includes a TET drive circuit 134 for controlling the application of power to the primary TET coil 130. The TET drive circuit 134 is controlled by a microprocessor 136 having an associated memory 138. A graphical user interface 140 is connected to the microprocessor 136 for inputting patient information, displaying data and physician instructions, and/or printing data and physician instructions. Through the user interface 140, a user such as the patient or a clinician can transmit an adjustment request to the physician and also enter reasons for the request. Additionally, the user interface 140 can enable the patient to read and respond to instructions from the physician and/or to alerts, as discussed further below.

The external portion 10b also includes a primary telemetry transceiver 142 for transmitting interrogation commands to and receiving response data, including sensed impedance data and sensed pressure data, from the implanted microcontroller 65. The primary transceiver 142 is electrically connected to the microprocessor 136 for inputting and receiving command and data signals. The primary transceiver 142 drives the telemetry coil 144 to resonate at a selected RF communication frequency. The resonating circuit can generate a downlink alternating magnetic field 146 that transmits command data to the microcontroller 65. Alternatively, the transceiver 142 can receive telemetry signals transmitted from a secondary TET/telemetry coil 114 in the internal portion 10a. Any or all portions of received data can be stored in the memory 138 associated with the microprocessor 136. A power supply 150 can supply energy to the control box 90 in order to power element(s) in the internal portion 10a. An ambient pressure sensor 152 is connected to microprocessor 136. The microprocessor 136 can use a signal from the ambient pressure sensor 152 to adjust received pressure measurements for variations in atmospheric pressure due to, for example, variations in barometric conditions or altitude, in order to increase the accuracy of pressure measurements.

FIG. 5 also shows the internal portion 10a including components which in this embodiment are included in the sensor housing 60, except for first and second sensor electrodes 72, 74 which are positioned on the band 20 as discussed below. As shown in FIG. 5, the secondary TET/telemetry coil 114 receives the power/communication signal 132 from the external antenna. The secondary coil 114 forms a tuned tank circuit that is inductively coupled with either the primary TET coil 130 to power the implant or the primary telemetry coil 144 to receive and transmit data. A telemetry transceiver 158 controls data exchange with the secondary coil 114. Additionally, the internal portion 10a includes a rectifier/power regulator 160, the microcontroller 65, a memory 162 associated with the microcontroller 65, a temperature sensor 112, the pressure sensor 62, the sensor electrodes 72, 74, and a signal conditioning circuit 164. The implanted components can transmit data (with or without adjustments due to temperature, etc.) from the sensor 62 and/or the electrodes 72, 74 to the control box 90 via the antenna (the primary TET coil 130 and the telemetry coil 144). Data can be stored in the memory 138, adjusted for ambient pressure, shown on a display on the control box 90, and/or transmitted, possibly in real time, to a remote monitoring station at a location remote from the patient.

Figure 6:
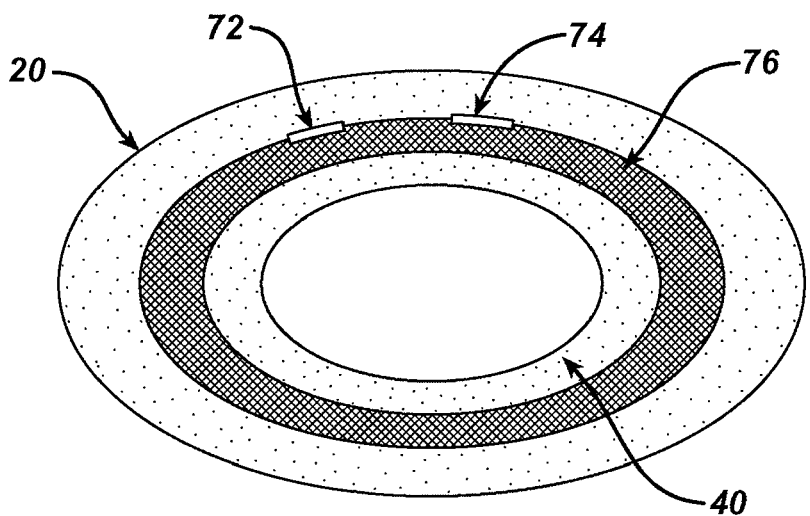
FIG. 6 is a schematic diagram of an embodiment of electrodes coupled to the food intake restriction device of FIG. 1A.

One embodiment of a gastric band 20 including the sensor electrodes 72, 74 disposed on a tissue-contacting surface of the gastric band 20 (e.g., in contact with fat tissue 76) is shown in FIG. 6. Generally, the electrodes 72, 74 can communicate measured data (wired or wirelessly) to an impedance measuring device, e.g., a processor such as the microcontroller 65, which can generally measure an impedance between the electrodes 72, 74. The microcontroller 65 can store any or all data received from the electrodes 72, 74 in the memory 162, analyze any or all of the data, and/or telemeter any or all of the data to an external device, e.g., the control box 90 via the reading device 70. While the electrodes 72, 74 in this illustrated embodiment are disposed on an outside surface of the band 20, the electrodes 72, 74 can be disposed elsewhere in the implanted portion 10a, with or without being disposed on a surface of the band 20. For example, the electrodes 72, 74 can be included as part of a dedicated sensing device disposed in the body to contact tissue. Moreover, the electrodes 72, 74 in this embodiment contact fat tissue 76 and gather data related to impedance of the fat tissue 76, but the electrodes 72, 74 can contact non-fat tissue (preferably, but not necessarily, in a position proximate to the restriction formed in the patient), and any sensed impedance data related to such tissue can be handled as discussed herein.

The electrodes 72, 74 can be made of any material capable of measuring impedance of tissue. The electrodes 72, 74 can be made from any biocompatible material appropriate for use in a body, such as a polymer, biocompatible metal, and other similar types of material. Non-limiting examples of materials include copper, gold, stainless steel, titanium, silver, and platinum-iridium (Pl—Ir). Furthermore, the electrodes 72, 74 can have any size and shape. Examples of the electrodes 72, 74 include electrodes widely used in and commercially available for pacemakers.

A coating can be used to insulate and waterproof the electrodes 72, 74 to avoid fluid seepage and potential short-circuiting of the electrodes 72, 74. The coating can be made from any biocompatible material appropriate for use in a body that will not interfere with the functionality of the electrodes 72, 74. By way of non-limiting example, suitable materials can include polyurethane, silicone, solvent-based polymer solutions, and any other polymer that will adhere to the electrodes 72, 74. Suitable techniques for applying the coating include spray-coating and dip-coating. The electrodes 72, 74 can be coated separately with different coatings or together in a single coating, and they can be coated before or after their disposal on a surface of the band 20. An adhesive or any other mating technique can be used to couple the electrodes 72, 74 fixedly or removably to the band 20.

Two electrodes 72, 74 are shown on the band 20, but any number of electrodes can be disposed on the band 20 (and/or other location in the implanted portion 10a). If the band 20 includes more than the two electrodes 72, 74, more than one impedance measurement can be made between different ones of the electrodes, communicated from the electrodes 72, 74 to the microcontroller 65, analyzed by the microcontroller 65, and/or communicated from the microcontroller 65 to an external device.

Figure 7:
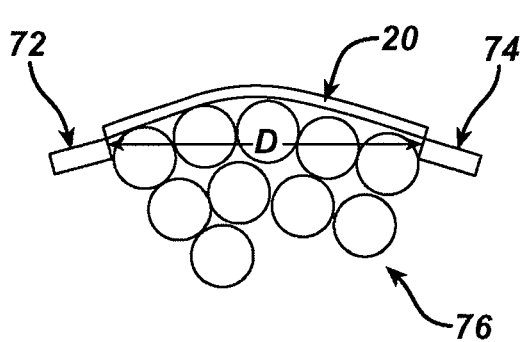
FIG. 7 is a partial view of the electrodes and the food intake restriction device of FIG. 6.
Figure 8:
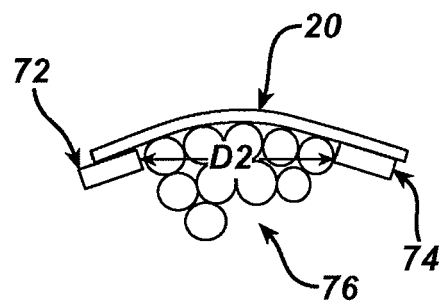
FIG. 8 is another partial view of the electrodes and the food intake restriction device of FIG. 6.

The electrodes 72, 74 can be aligned linearly at an initial, fixed distance D, as shown in FIG. 7. As the patient loses weight, the fat tissue 76 can decrease in size (as fat cells in the fat tissue 76 shrink), thereby drawing the electrodes 72, 74 closer together (e.g., to a distance D2, as shown in FIG. 8, that is shorter than the initial distance D) and accordingly change an impedance between the electrodes 72, 74. The initial, fixed distance D should therefore allow for the electrodes 72, 74 to remain a distance apart (e.g., not come into contact with each other) as the patient loses weight. However, in some embodiments, the distance between the electrodes 72, 74 can be adjusted in position, e.g., by moving the electrodes 72, 74 to a different location on the surface of the band 20, by replacing the band 20 with a band having differently spaced electrodes 72, 74, by implanting one or more additional electrodes, etc. The larger the distance between the electrodes 72, 74, typically the stronger the electrode potentials. In a configuration containing more than the two electrodes 72, 74, impedance measurements can be taken between non-adjacent electrodes, thereby allowing the distance D to be altered without physically changing the location of any electrodes. Alternatively, changes in capacitance can be measured between the electrodes 72, 74 by measuring changes in resonant excitation frequency between the electrodes 72, 74, as discussed further below.

In use, the electrodes 72, 74 can gather data and transmit measured signals to the microcontroller 65. The electrodes 72, 74 can provide data at any update rate, such as approximately 20 Hz, as in this embodiment. Such a rate can provide a telemetry/TET mode cycle completion at approximately every 50 ms. For example, the TET/telemetry coil 114 can provide TET for the sensor housing 60 for approximately 45 ms to power the sensor housing 60 and then provide telemetry of data for approximately 5 ms. Of course, any other switching topology can be used. For example, because impedance of the tissue 76 typically changes slowly over time, automated telemetry of impedance data can be provided at a slow rate, e.g., once per day, even if the microcontroller 65 transmits other gathered data at a faster or slower rate. It will also be appreciated that switching between TET and telemetry may be unnecessary. For example, the sensor housing 60 can be active, such that TET is not required. As another example, a second coil (not shown) can be added to the sensor housing 60, with one of the coils in the sensor housing 60 being dedicated to TET and the other to telemetry.

Figure 9:
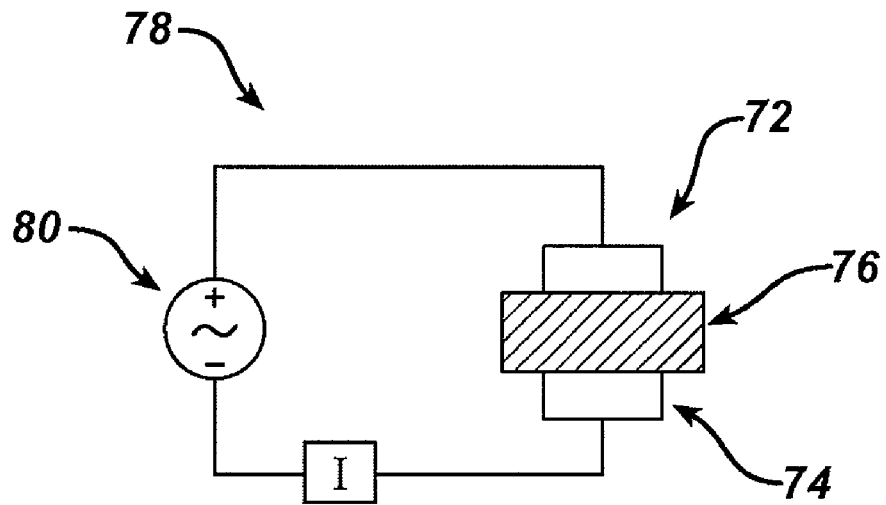
FIG. 9 is an embodiment of a circuit including a voltage excitation source.
Figure 10:
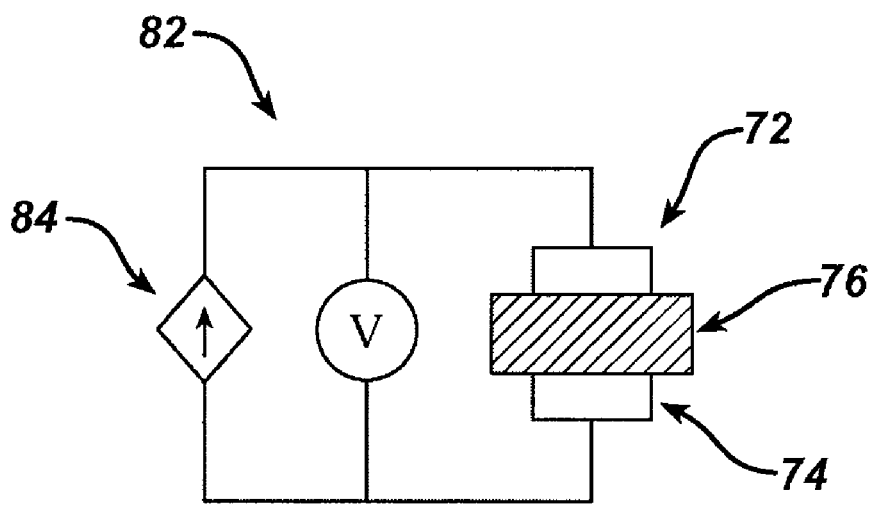
FIG. 10 is an embodiment of a circuit including a current excitation source.

The electrodes 72, 74 can gather impedance data in a variety of ways. Exemplary impedance measuring systems that can be used to measure impedance of a tissue are disclosed in more detail in commonly-owned U.S. Pat. No. 5,817,093, which is hereby incorporated by reference. Generally, the tissue 76 can be stimulated by a voltage or current excitation source to create an electrical field around and/or between the electrodes 72, 74, and impedance can be calculated from the resulting current and voltage, where $|Z|=V_{rms}/I_{rms}$. In this embodiment, one frequency is used to excite the tissue 76 (typically a frequency outside the range of neuromuscular stimulation), but multiple frequencies can be used, which can increase accuracy of impedance measurements by allowing a spectral response of tissue impedance to be gathered. The excitation source can be included in the implantable portion 10a or in the external portion 1b (e.g., provided by the control box 90 through the reading device 70). In some embodiments, the electrodes 72, 74 can be stimulated using both implanted and external excitation sources to, for example, allow the electrodes 72, 74 to automatically gather data when excited by an internal source and to gather data on request when excited by an external source. To gather data automatically, the electrodes 72, 74 should be provided with power (e.g., from a power source such as a battery or a capacitor included in the implantable portion 10a). FIG. 9 illustrates one example circuit 78 including an AC/DC voltage source 80 that can be used to excite the tissue 76 and allow current to be measured between the electrodes 72, 74. FIG. 10 illustrates another example circuit 80 including a current source 84 that can be used to excite the tissue 76 and allow voltage to be measured between the electrodes 72, 74. Still other alternatives and variations will be appreciated by those skilled in the art.

Having received sensed data from the electrodes 72, 74, the microcontroller 65 can store any or all portions of the data in the memory 162. Any type of memory can be used for the memory 162, including but not limited to one or more of volatile (e.g., SRAM, etc.), non-volatile (e.g., flash, hard drive, etc.), or other memory. Furthermore, the memory 162 can be used to store pre-selected information or pre-selected types of information. For example, the memory 162 can store maximum, minimum, and baseline measurement data (for impedance, pressure, etc.), pressure measurements, patient weight, fluoroscopic images or video of a patient swallowing, and/or any other information suitable for storing in the memory 162 as will be appreciated by those skilled in the art.

The microcontroller 65 can analyze data received from the electrodes 72, 74 in a variety of ways in any combination with each other, or independently, depending on the microcontroller's programming. Typically, the microcontroller 65 analyzes a sequence of data values measured over a period of time rather than analyzing every discrete measurement, thereby allowing analysis of trends over time and saving processing resources by not necessarily having to continually analyze incoming data. The microcontroller 65 can, however, evaluate discrete data measurements (and/or a range of data) for invalid data and determine to discard any invalid data. Furthermore, the microcontroller 65 can store all sensed data it receives in the memory 162 and subsequently analyze any portion of it at any frequency of analysis, e.g., analyze stored data every "X" minutes, at times corresponding to detected changes in pressure, and upon signal from an external device. The microcontroller 65 can store all of the measurements received from the electrodes 72, 74 for transmission to an external device but only compute impedance on a sampling of the measurements.

Analyzing impedance data can include, for example, measuring impedance using data from the electrodes 72, 74. The microcontroller 65 can measure impedance by inferring impedance from some or all of the measurements received from the electrodes 72, 74, such as by determining a voltage difference between the two electrodes 72, 74 if the electrodes 72, 74 transmit voltage data to the microcontroller 65. As another example, the microcontroller 65 can analyze the data by comparing the impedance measured between the electrodes 72, 74 with a range of impedance values, thereby forming a closed-loop feedback system. The microcontroller 65 can determine if each of the impedance readings varies from a threshold impedance value, typically indicative of a normal or baseline impedance. The range of impedance values and/or the threshold impedance value that the microcontroller 65 compares with measured impedance value(s) are typically programmed into the microcontroller 65 by a physician based on historical performance in the patient, based on an impedance reading taken upon implantation of the band 20 in the patient or shortly thereafter, or, particularly for patients having recently implanted bands, in a typical patient. The range of impedance values and the threshold impedance value for a patient can change over time, e.g., as the patient gains or loses weight, and different patients can have different ranges and threshold values. If the impedance reading is greater than or equal to the threshold value (or less than or equal to the threshold value, depending on the threshold value), or if the impedance falls outside the range of impedance values, then the measured impedance may indicate a potentially significant event for analysis purposes, e.g., a change in band pressure, a change in tissue configuration, weight change, band slippage, tissue erosion, an electronic error, etc.

The microcontroller 65 can also determine whether any data triggers an alarm or alert. Data can trigger an alert in a variety of ways, and one or more conditions triggering an alert can be programmed into the microcontroller 65. Such conditions can vary by patient and can change over time for a particular patient, such as if the patient's treatment plan changes or when the patient gains or loses weight. For example, if the microcontroller 65 determines that any impedance data falls outside a range of impedance values and/or is more or less than a threshold impedance value, then the microcontroller 65 can provide an alert to a physician, the patient, and/or to any number of other people because such outlying impedance data can indicate a possible internal problem or a physical change in the patient (e.g., weight gain or loss) that can indicate a need to adjust the patient's treatment plan (e.g., an internal adjustment such as a change a volume of fluid in the band 20, or an external adjustment such as advising the patient to change an amount of physical activity or changing the patient's nutritional plan). As another example, the microcontroller 65 can determine that measured impedance values over a period of time are substantially constant, typically indicative of a substantially unchanged amount of tissue between the electrodes 72, 74 and a weight loss plateau. Triggering an alert to provide notice of such a plateau can, for instance, help a physician determine any appropriate changes to a patient's treatment plan (e.g., an internal adjustment such as adjusting pressure of the band 20, or an external adjustment such as advising the patient to eat less).

Figure 11:
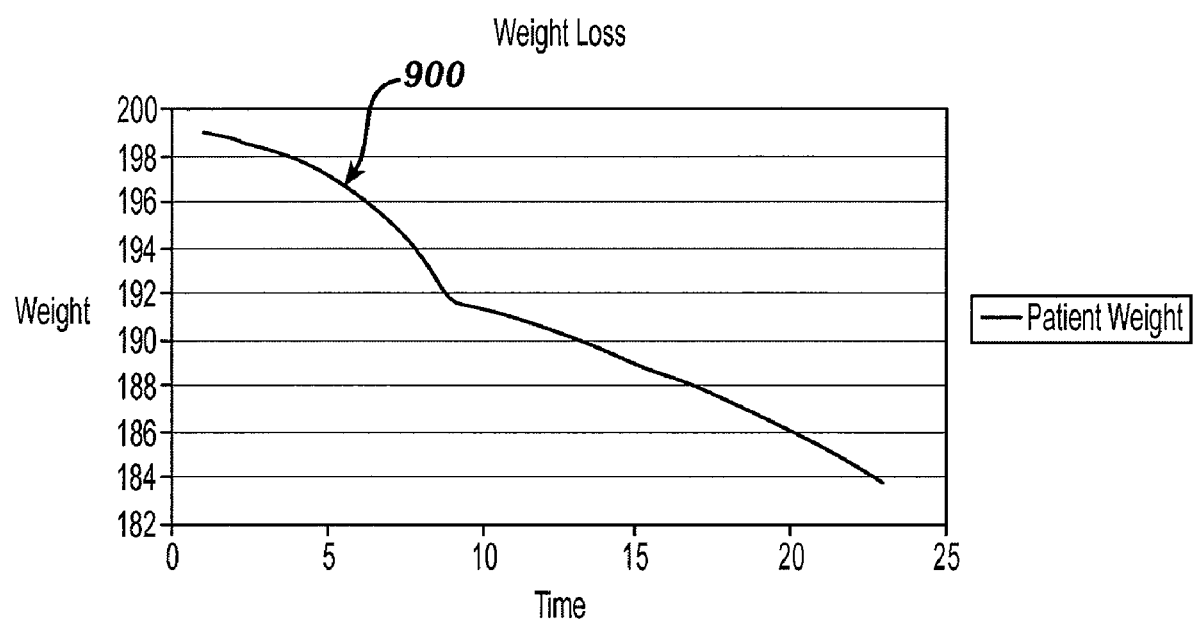
FIG. 11 is a graphical representation of an embodiment of a measured inflection in a patient's weight loss.

In another example, the microcontroller 65 can analyze gathered data related to a weight of a patient (e.g., impedance of the fat tissue 76, a weight of the patient at various sequential times, pressure data, and any combination of these or other data related to the patient's weight) for an inflection in a plot line. FIG. 11 illustrates an example of such a plot line 900 indicating a reduction of a fat pad of the patient to its minimized size, where an inflection in patient weight occurs at about weight 192 and time 9. (The weights, times, and inflection in FIG. 11 are examples only.) An inflection in the plot line 900 can indicate a minimization of the fat tissue 76 and that the patient's treatment plan should be adjusted (e.g., an internal adjustment such as tightening the band 20 to account for the lost fat). In some embodiments, the microcontroller 65 can generate the plot line 900 from one set of data values (e.g., the patient's weight, as shown in FIG. 11) and use one or more additional sets of data values (e.g., sensed data such as pressure and impedance) to corroborate an inflection in the plot line 900. If so corroborated by one or more additional sets of data values, the microcontroller 65 can trigger an alert.

Figure 12:
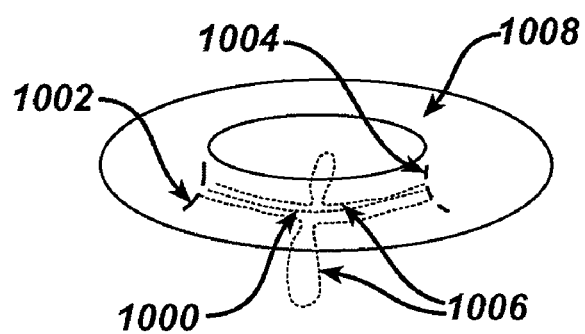
FIG. 12 is a schematic diagram of an embodiment of electrodes in contact with tissue.

In still another example, the microcontroller 65 can determine if measured impedance has increased since a previously measured impedance, typically an immediately preceding measured impedance. Increased impedance generally corresponds to a larger distance between the electrodes 72, 74 because current travels through more tissue on a longer path. Increased impedance can be caused by, for example, patient weight gain (increase in fat cell size) or a change in configuration of the fat tissue 76 between the electrodes 72, 74 (more tissue between the electrodes 72, 74 caused by, e.g., a fold in tissue or a bolus of food). Likewise, decreased impedance can be caused by, for example, patient weight loss or a reduction in tissue between the electrodes 72, 74. FIG. 12 illustrates another embodiment of a restriction system showing a normal impedance path 1000 between one set of electrodes 1002 and an opposed set of electrodes 1004 and altered impedance paths 1006 between the electrodes 1002, 1004 due to a fold in tissue 1008 or bolus of food. Referring again to the previously discussed embodiment, because a change in configuration of the fat tissue 76 typically results in a sudden impedance increase, as opposed to an asymptotic increase typically associated with gradual weight gain, the microcontroller 65 can be configured to detect a sudden increase in impedance. A change in tissue configuration can be non-invasively corroborated with the microcontroller 65 by, for example, analyzing one or more additional data values, such as pressure data gathered by the sensor 62. If the sensor 62 detected a pressure rise corresponding to the time of a sudden increase in impedance, the microcontroller 65 can conclude that the fat tissue 76 changed configuration and accordingly trigger an alert.

The microcontroller 65 can provide an alert by, for example, communicating a signal to an external device (e.g., the control box 90) indicating the relevant data and triggering notice of the alert. An alert can include any one or more of the following: an e-mail, a phone call, a text message, an audible signal, a message displayed on an external device, or any other type of alert. Two or more alerts can be provided to multiple people under similar conditions, although alerts may not be provided simultaneously to multiple people. The conditions for and/or the type of an alert can also vary relative to the recipient of the alert. For example, with respect to alerts for physicians, such alerts may be limited to those provided upon an event indicating maladjusted electrodes 72, 74, such as due to a fold in the tissue 76 that the patient could not correct by swallowing a bolus of food in an attempt to return the band 20 to normal peristaltic pressure. With respect to alerts for patients, such alerts may be limited to patient activity such as those provided upon an indication that the patient is losing or gaining weight. A variety of other conditions under which alerts can be directed to a physician, a patient, and/or another person will be understood by those skilled in the art. Other suitable processes for detecting alert triggers, as well as ways in which the alerts can be provided, will be appreciated by those skilled in the art.

Data stored in the memory 162 can be communicated to an external device. In some embodiments, the microcontroller 65 continually communicates data (via the telemetry transceiver 158 and the secondary coil 114), and the data is only received when an appropriate receiving device, such as the antenna (the primary TET coil 130 and the telemetry coil 144), moves into sufficient proximity of it. In some embodiments, a download of data from the memory 162 can be triggered 416 when an external device (e.g., the reading device 70) telemetrically provides power to the sensor housing 60, e.g., when the external device is moved in proximity of the sensor housing 60. The external device can be mobile (e.g., a wand or hand-held unit that can be waved or otherwise placed in proximity of the sensor housing 60) or stationary (e.g., a bedside, desk-mounted, or car-mounted box that the patient can move near). Telemetrically providing power to the sensor housing 60 can save power in the internal portion 10*a* because download communication power is supplied by the external portion 10*b*.

The external device can be configured to store data received from the sensor housing 60. The external device can be further configured to communicate the data to another external device, such as a base unit at a location remote from the patient. The external device (typically, the control box 90 or other device having a capability to display or otherwise provide an alert) can detect if the internal portion 10*a* communicated a signal indicating an alert and provide an alert as appropriate (e.g., displaying a warning notice, sending an e-mail message, etc.).

Figure 13:
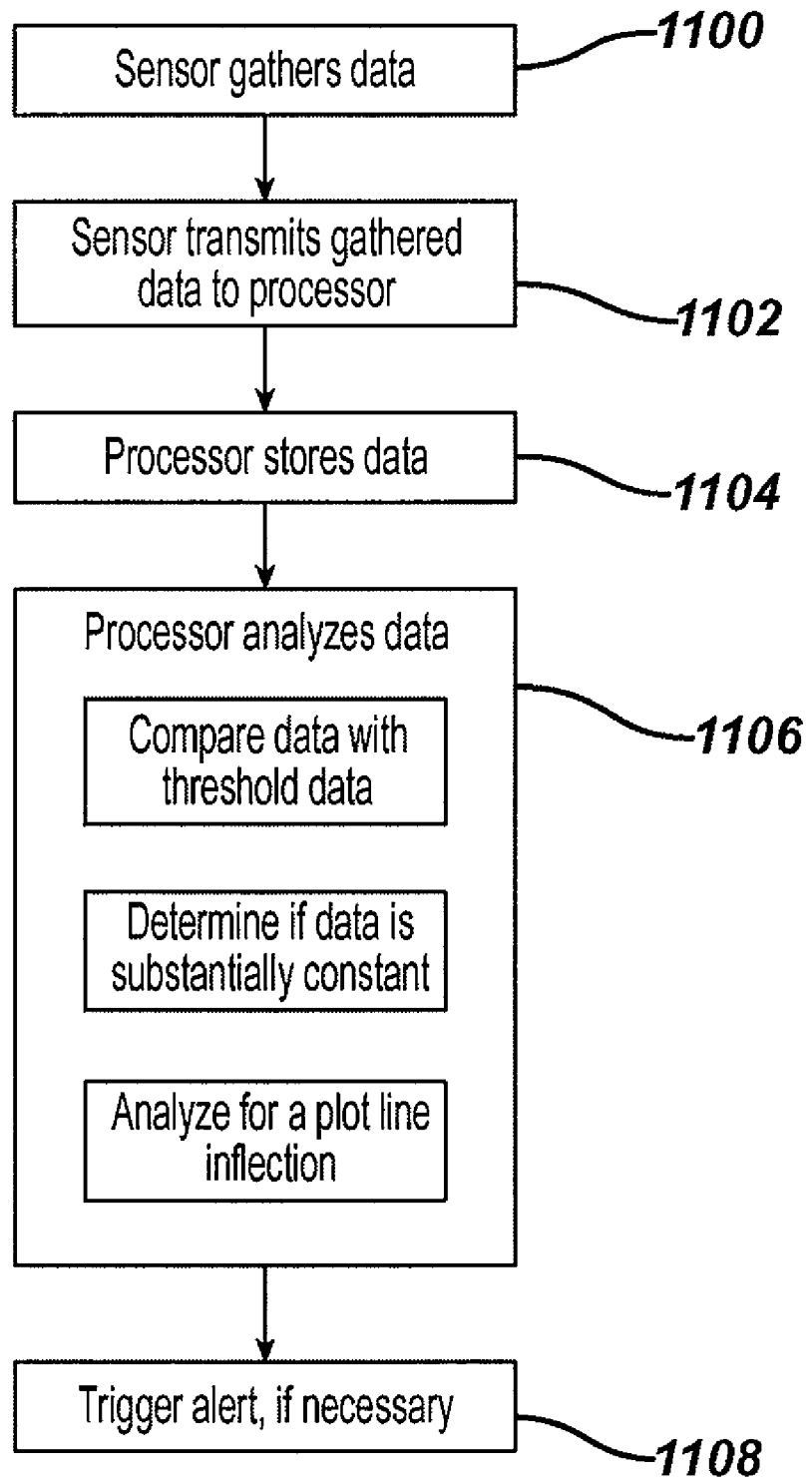
FIG. 13 is a flow diagram showing an embodiment of a data analysis protocol for data gathered by the electrodes of FIG. 6.

As illustrated in one embodiment of a process shown in FIG. 13, in use, a sensor can generally gather data related to the restriction formed by the band 20 and the microcontroller 65 can analyze the sensed data to determine if the sensed data varies from a baseline or typical data. The microcontroller 65 can also provide an alert to the control box 90 (e.g., through the reading device 70) indicating the variation, which the control box 90 can provide to a user by, for example, displaying the alert (e.g., using the user interface 140). Such detection and notification of a data variation can provide a patient, a physician, and/or any other user with evaluations of the efficacy of the band 20, including possible solutions to correct for any undesirable sensed data, thereby allowing for improved functionality of the band, for timely (possibly in real time) attention to problems before they worsen or adversely affect patient morale, and/or for other diagnostic or treatment advantages.

While the process shown in FIG. 13 is discussed with relation to analyzing impedance and to the elements included in FIGS. 1A-8, a person skilled in the art will appreciate that the process can be modified to include more or fewer elements, reorganized or not, and can be performed in the system 10 or in another, similar system having other, similar elements. The electrodes 72, 74 measure impedance of the fat tissue 76 in this embodiment, but any tissue impedance can be handled as discussed herein. The microcontroller 65 processes instructions in this embodiment, but any processor configured to process instructions for a system (e.g., a central processing unit, a microprocessor, a state machine, application specific integrated circuits (ASICs), an analog computer, an optical or photonic computer, logic circuitry, etc.) can be used. Furthermore, the sensor 62 in this illustrated embodiment measures fluid pressure, but any sensed pressure data related to the band 20 can be handled as discussed herein.

The electrodes 72, 74 can gather 1100 data related to the impedance of the tissue 76. An electrical field can be applied around the electrodes 72, 74 so impedance of the fat tissue 76 can be measured with the electrodes 72, 74. The electrical field can be applied in any way, such as via an excitation source disposed in the sensor housing 60 (e.g., on the same circuit board as the microcontroller 65) that can supply the electrodes 72, 74 with a time-varying signal, e.g., alternating current. The electrodes 72, 74 can transmit 1102 gathered data to the microcontroller 65. Having received sensed data, the microcontroller 65 can, as discussed above, store 1104 the data, analyze 1106 the data, and, if necessary, trigger 1108 an alert.

Figure 14:
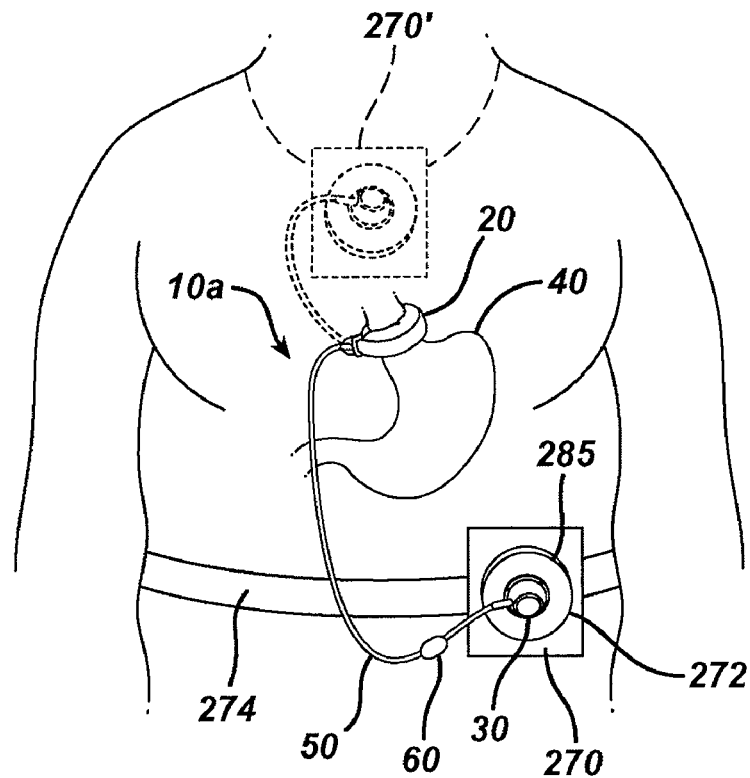
FIG. 14 is a schematic diagram of an embodiment of a data logger for recording pressure measurements related to the food intake restriction device of FIG. 1A.

As mentioned above, a pressure history (e.g., pressure data gathered by the sensor 62), an impedance history (e.g., impedance data gathered by the electrodes 72, 74), and/or other data can be uploaded to the control box 90 (and/or other units located local or remote to the patient) to allow a person to physically evaluate and/or electronically evaluate the patient's treatment and/or performance of elements included in the internal portion 10a over a designated time period. FIG. 14 illustrates an embodiment of an external device, a data logger 270, that can be used as an external storage mechanism to store impedance measurements, pressure measurements, and/or any other data over a period of time. The data logger 270 can function as a removably attached reading device 70, mentioned above. In this example, the data logger 270 includes a wearable pack external to the patient worn on a belt 274 and positioned over or within communication range of the region(s) where element(s) the data logger 270 may communicate with are implanted within the patient. Alternatively, the data logger 270 can be worn about the patient's neck, as shown by a device 270', such as when the injection port 30 is implanted on the patient's sternum and the port 30 includes the pressure sensing device. In another embodiment, the data logger 270 is also implanted within the patient.

As shown in FIG. 14, the data logger 270 includes a TET coil 285 and a telemetry coil 272 which can be worn by the patient so as to lie adjacent to the internal portion 10a. The TET coil 285 can provide power to the implant, while the telemetry coil 272 can interrogate the implant and can receive data signals, including pressure measurements and impedance measurements, through the secondary telemetry coil 114 in the implanted portion 10a. In another embodiment, the TET coil 285 and the telemetry coil 272 can be consolidated into a single coil and alternate between TET and telemetry functions at any suitable rate for any suitable durations.

Impedance of tissue can be repeatedly measured, measured at regular intervals, measured upon a signal from the microcontroller 65, and/or at any other interval understood by those skilled in the art. Impedance measurements can similarly be transmitted to the data logger 270 at any update rate sufficient to monitor impedance.

The pressure within the band 20 can be repeatedly sensed and transmitted to the data logger 270 at an update rate sufficient to measure peristaltic pulses against the band 20. Typically, this update rate is in the range of 10-20 pressure measurements per second, but any update range can be used. The data logger 270 is typically worn during waking periods to record pressure variations during the patient's meals and daily routines. At the end of the day, or another set time period, the data logger 270 can be removed and recorded pressure data downloaded to the external memory 138. The pressure history can be uploaded from the memory 138 to a remote unit over one or more communication links during a subsequent communication session. Alternatively, pressure data can be directly uploaded from the data logger 270 to a remote unit using one or more communication links. A communication link can include any single or combination of two or more data transmission media including web-based systems utilizing high-speed cable or dial-up connections, public telephone lines, wireless RF networks, Bluetooth, ultrawideband (UWB), satellite, T1 lines or any other type of communication media suitable for transmitting data between remote locations. The data logger 270 can be configured to dock into another device, e.g., a docking station, that is configured to receive data communication from the data logger 270 and transmit the received data to a remote unit.

Figure 15:
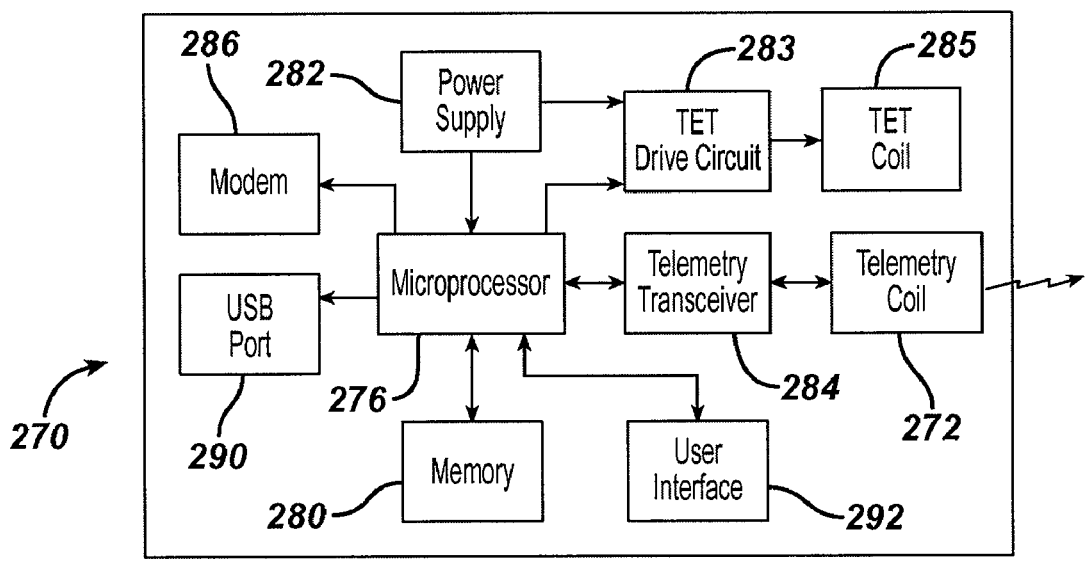
FIG. 15 is a block diagram showing an embodiment of components of the data logger of FIG. 14.

FIG. 15 shows the data logger 270 in greater detail. As shown in FIG. 15, the data logger 270 includes a microprocessor 276 for controlling telemetry communications with the internal portion 10a. The microprocessor 276 is connected to a memory 280 for storing data from the internal portion 10a. In this embodiment, the memory 280 includes forty Mb of SRAM and is configured to store one hundred hours of time stamped pressure data, but any other type of storage can be used, and the memory 280 can store any amount of and any type of data. By way of non-limiting example, any other type of volatile memory or any type of non-volatile memory can be used, including but not limited to flash memory, hard drive memory, etc. While the data logger 270 in this example is operational, data can be read and stored in the memory 280 at a designated data rate controlled by the microprocessor 276.

The microprocessor 276 can be energized by a power supply 282. In one embodiment, the power supply 282 includes a rechargeable cell (not shown), such as a rechargeable battery. In some embodiments, the rechargeable cell is removable and can be recharged using a recharging unit and replaced with another rechargeable cell while the spent cell is recharging. In other embodiments, the rechargeable cell can be recharged by plugging a recharging adapter into the data logger 270 and a wall unit. In yet another embodiment, the rechargeable cell can be recharged wirelessly by a wireless recharging unit. In still another embodiment, the power supply 282 includes an ultra capacitor, which can also be recharged. Of course, any other type of power supply can be used.

To record pressure, the microprocessor 276 can initially transmit a power signal to the internal portion 10a via a TET drive circuit 283 and the TET coil 285. After transmitting the power signal, the microprocessor 276 can transmit an interrogation signal to the internal portion 10a via a telemetry transceiver 284 and the telemetry coil 272. The interrogation signal can be intercepted by the telemetry coil 114 and transmitted to the microcontroller 65. The microcontroller 65 can send a responsive data signal, such as an impedance reading from the sensors 72, 74 or an optionally-temperature-adjusted pressure reading from the sensor 62, via the transceiver 158 and the secondary telemetry coil 114. The data signal can be received through the telemetry coil 272 and directed by the transceiver 284 to the microprocessor 276. The microprocessor 276 can store the data and initiate the next interrogation request. If applicable, the microprocessor 276 can also respond to an alert identified by the microcontroller 65, such as with a visual alert (e.g., flashing a light on the data logger 270, displaying a message on a user interface 292, etc.) and/or with an audible alert. The user interface 292 can include any number and types of features, including but not limited to a speaker, an LED, an LCD display, an on/off switch, etc. In some embodiments, the user interface 292 is configured to provide only output to the patient and does not permit the patient to provide input to the data logger 270. The user interface 292 thus includes an LED, which when lit shows that the power supply 282 is sufficiently charged and another, differently colored LED to show when the power supply 282 needs to be recharged, although such power indicators can be shown using any type and any combination of indicators such as one light that illuminates upon low power charge, an audible alert, an email alert, etc. In other embodiments, the user interface 292 can allow the patient to provide input to the data logger 270 and can accordingly include any suitable components and features.

When finished measuring and recording data, the data logger 270 can be removed from the patient and/or from the belt 274 and recorded data can be downloaded to the control box 90 (and/or to any other external device). The data logger 270 can include a modem 286 for transmitting data directly to a remote base unit using a communication link. For example, the patient can connect the modem 286 to a telephone line (or other communication link), dial the physician's modem (if necessary), and select a "send" button on the user interface 292. Once connected, the microprocessor 276 can transmit stored pressure history through the phone line to a microprocessor included in the remote unit. Alternatively, the data logger 270 can include a USB port 290 for connecting the logger 270 to the control box 90. The logger USB port 290 can be connected to a USB port included on the control box 90 and the "send" switch activated to download data to the memory 138 in the control box 90. After data is downloaded, the logger 270 can be turned off through the user interface 292 or reset and placed back on the patient and/or the belt 274 for continued measurements.

Figure 16:
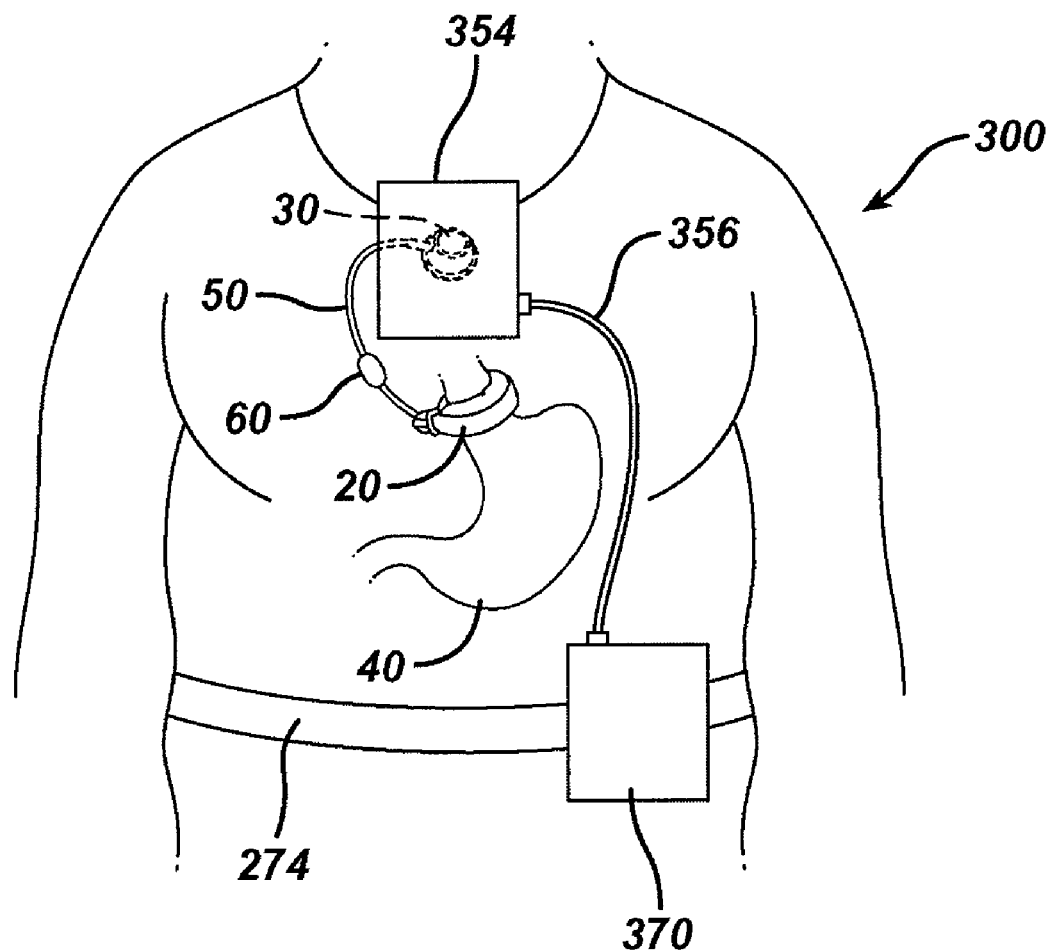
FIG. 16 is a schematic diagram of an embodiment of a data logging system for recording pressure measurements related to the food intake restriction device of FIG. 1A.

An alternate embodiment of a data logging system 300 is shown in FIG. 16. In this example, the data logging system 300 includes a coil head 354 and a data logger 370. The coil head 354 and the data logger 370 are in communication via a detachable cable 356. Any one or more suitable alternative communication links can be used in the place of the cable 356, including but not limited to a wireless transmitter/receiver system. In the illustrated embodiment, the coil head 354 is worn around the neck of the patient and is positioned generally over the injection port 30 and within communication range of the sensor housing 60. The data logger 370 is worn on the belt 274 about the patient's waist. Of course, these respective locations are merely exemplary, and either or both the coil head 354 and the data logger 370 can be positioned elsewhere. By way of non-limiting example, when the injection port 30 is implanted in the patient's abdomen, the coil head 354 can be worn on the belt 274. The coil head 354 and the data logger 370 are represented as simple blocks in FIG. 16 for illustrative purposes only, and either of the coil head 354 or the data logger 370 can be provided in a variety of shapes, sizes, and configurations.

Figure 17:
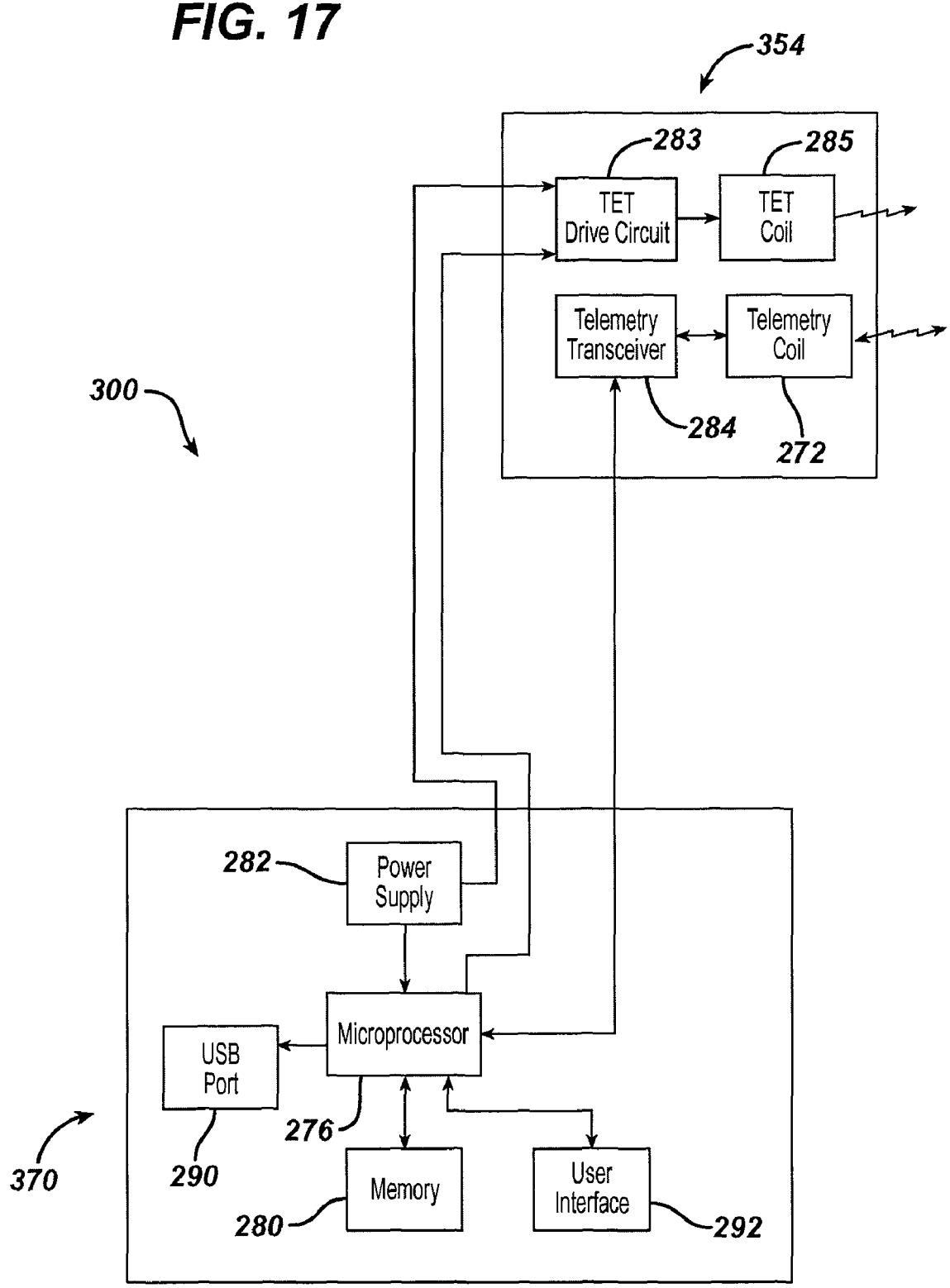
FIG. 17 is a block diagram showing an embodiment of components of the data logging system of FIG. 16.

Exemplary components of the data logging system 300 are shown in FIG. 17. As shown, the data logger 370 includes the microprocessor 276, the memory 280, the power supply 282, the USB port 290, and the user interface 292. The coil head 354 includes the TET drive circuit 283, the telemetry transceiver 284, the TET coil 285, and the telemetry coil 272. The TET drive circuit 283 is configured to receive power from the power supply 282 via the cable 356. The TET drive circuit 283 is further configured to receive signals from the microprocessor 276 via the cable 356. The telemetry transceiver 284 is configured to receive signals from the microprocessor 276 and transmit signals to the microprocessor 276, via the cable 356. In another embodiment, the telemetry transceiver 284 is configured to only transmit signals to the microprocessor 276. The above discussion of such components with reference to FIG. 15 can also be applied to the components shown in FIG. 17. In the embodiment illustrated in FIG. 17, the coil head 354 and the data logger 370 can be viewed as a separation of components including the data logger 270 (described above) into two physically separate units. It will be appreciated by a person skilled in the art that any of the components shown in FIG. 17, as well as their relationships, functions, etc., can be varied in any suitable way.

In the present example, the coil head 354 is configured similar to and functions in a manner similar to the antenna (the primary TET coil 130 and the telemetry coil 144) described above. The TET coil 285 of coil head 354 is configured to provide power to the injection port 30. Of course, to the extent that any other devices (e.g., a pump, etc.) are implanted in the patient that are configured to receive power from the TET coil 285, the TET coil 285 can also provide power to such devices. Power provided by the TET coil 285 can be provided to the TET coil 285 by and regulated by the TET drive circuit 285, which can itself receive power from the power supply 282 via the cable 356. Such power provided to the TET drive circuit 283 can be regulated by the microprocessor 276 via the cable 356. In addition, or in the alternative, the microprocessor 276 can regulate the manner in which the TET drive circuit 285 provides power to the TET coil 285. While the present example contemplates the use of RF signaling through the TET coil 285, any other type of powering technique, as well as alternative power communicators, can be used. Other suitable configurations and relationships between these components, as well as alternative ways in which they may operate, will be appreciated by those skilled in the art.

The telemetry coil 272 of the coil head 354 is configured to receive signals from the coil 114, including signals indicative of impedance in the system 10 (e.g., impedance of fat tissue, impedance of stomach tissue, impedance of esophageal tissue, etc.), signals indicative of the pressure within the implanted band system (e.g., pressure of fluid within the injection port 30, within the catheter 50, and/or within the adjustable band 20, pressure obtained using the pressure sensor 62, etc.), signals indicative of temperature, and/or any other type of signal representing any other type of information from any other source. Signals received by the telemetry coil 272 can be communicated to the telemetry transceiver 284, which can communicate such signals to the microprocessor 276 via the cable 356. The telemetry transceiver 284 can perform any appropriate translation or processing of signals received from the telemetry coil 272 before communicating signals to the microprocessor 276. Other suitable configurations and relationships between these components, as well as alternative ways in which they may operate, will be appreciated by those skilled in the art. It will also be appreciated that components may be combined. By way of non-limiting example, the TET coil 285 and the telemetry coil 272 can be consolidated into a single coil and alternate between TET and telemetry functions at any suitable rate for any suitable durations. In addition, while the present example contemplates the use of RF signaling through the telemetry coil 272, it will be appreciated that any other type of communication technique (e.g., ultrasonic, magnetic, etc.), as well as alternative communicators other than a coil, can be used.

In one exemplary use, the patient wears the coil head 354 and the data logger 370 throughout the day to record data in the memory 280. At night, the patient can decouple the data logger 370 from the coil head 354 and couple the data logger 370 with a docking station, e.g., the control box 90. While the data logger 370 and the control box 90 are coupled, the control box 90 can transmit data received from the data logger 370 to a remote unit. To the extent that the power supply 282 includes a rechargeable cell, the control box 90 can recharge the cell while the data logger 370 is coupled with the control box 90. However, a patient need not necessarily decouple the data logger 370 from the coil head 354 in order to couple the data logger 370 with the control box 90. Moreover, data such as impedance and pressure measurements can be recorded in the memory 280 during the night in addition to or as an alternative to recording such measurements during the day, and data can be recorded twenty-four hours a day. In that way, timing of measurement taking and recordation need not be limited to the daytime only.

As described above, the data logger 370 can receive, store, and communicate data relating to impedance and to pressure within the restriction system. However, the data logger 370 can receive, store, and/or communicate a variety of other types of data. By way of non-limiting example, the data logger 370 can also receive, process, store, and/or communicate data relating to temperature, EKG measurements, eating frequency of the patient, the size of meals eaten by the patient, the amount of walking done by the patient, etc. It will therefore be appreciated by those skilled in the art that the data logger 370 can be configured to process received data to create additional data for communicating to the control box 90. For example, the data logger 370 can process impedance data obtained via the coil head 354 to create data indicative of weight lost by the patient and pressure data obtained via the coil head 354 to create data indicative of the eating frequency of the patient. It will also be appreciated by those skilled in the art that the data logger 370 can include additional components to obtain non-pressure, non-impedance data. For example, the data logger 370 can include a pedometer or accelerometer (not shown) to obtain data relating to the amount of walking done by the patient. Data obtained by such additional components can be stored in the memory 280 and communicated to the control box 90 in a manner similar to that described above. The data logger 370 can also include components for obtaining data to be factored in with internal pressure measurements to account for effects of various conditions on the pressure. For example, the data logger 370 can include a barometer for measuring atmospheric pressure. In some embodiments, the data logger 370 includes an inclinometer or similar device to determine the angle at which the patient is oriented (e.g., standing, lying down, etc.), which can be factored into pressure data to account for hydrostatic pressure effects caused by a patient's orientation. Alternatively, an inclinometer or other device for obtaining non-pressure data can be physically separate from the data logger 370 (e.g., implanted). Still other types of data, ways in which such data may be obtained, and ways in which such data may be used will be appreciated by those skilled in the art.

It will also be appreciated by those skilled in the art that one or more embodiments described herein can enable health care providers or others to use impedance and/or pressure data as a feedback mechanism to identify, train, and/or prescribe dietary advice to a patient. Such a feedback mechanism can provide data or otherwise be used in multiple ways. For example, pressure feedback can be obtained when a patient swallows a particular food portion, and based on such pressure feedback, the patient can be advised or taught to eat smaller portions, larger portions, or portions equal to the portion tested. Of course, a food portion so prescribed can be tested by evaluating pressure feedback obtained when the patient swallows the prescribed food portion, such that a food portion prescription may be refined through reiteration. As another example, impedance measurements of fat tissue can be used to correlate between fat pad size and one or more patient characteristics such as a patient weight loss profile or weight loss speed. As yet another example, a patient can test desired foods for appropriateness based on pressure feedback together with portion size and/or based on any other parameters. It will also be appreciated by those skilled in the art that continuous impedance and/or pressure data monitoring can be used locally and/or remotely to enable portion size monitoring, food consistency monitoring (e.g., liquids vs. solids), eating frequency, and/or other patient activities.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A restriction system for forming a restriction in a patient, comprising:
    an implantable restriction device configured to form a restriction in a patient;
    at least two sensor electrodes disposed on a tissue-contacting surface of the implantable restriction device; and
    an impedance measuring device configured to be in electronic communication with the sensor electrodes and to measure an impedance between the sensor electrodes, wherein the impedance measuring device is configured to
        measure the impedance between the sensor electrodes over a period of time to gather a sequence of impedance values, and generate a plot line from the sequence of impedance values indicating a weight of the patient over the period of time.

2. The system of claim 1, wherein the implantable restriction device comprises an adjustable gastric band.

3. The system of claim 1, wherein the impedance measuring device is configured to compare an impedance measured between the sensor electrodes with a range of impedance values.

4. The system of claim 1, wherein the sensor electrodes are configured to be in contact with tissue proximate to the restriction formed by the implantable restriction device, and wherein the impedance measuring device is configured to measure the impedance of the tissue.

5. The system of claim 1, wherein the impedance measuring device is configured to signal for a corrective action if the impedance measuring device measures an impedance between the sensor electrodes that differs from a threshold impedance value.

6. The system of claim 5, wherein the threshold impedance value reflects a baseline amount of tissue proximate to the restriction formed by the implantable restriction device.

7. The system of claim 5, wherein a measured impedance value between the sensor electrodes that differs from a threshold impedance value indicates either patient weight loss or patient weight gain.

8. The system of claim 5, wherein the impedance measuring device is configured to determine if measured impedance values gathered over the period of time are each at a substantially constant value indicative of a weight loss plateau.

9. The system of claim 5, wherein the corrective action includes suggesting a change in pressure within the implantable restriction device.

10. The system of claim 5, wherein the corrective action includes suggesting a modification of the patient's treatment plan.

11. The system of claim 1, wherein the impedance measuring device is configured to determine a trend of patient weight loss if the plot line indicates an asymptotic decrease in the impedance over the period of time, and to determine that the trend is patient weight gain if the plot line indicates an asymptotic increase in the impedance over the period of time.

12. The system of claim 11, wherein the impedance measuring device is configured to
    detect a sudden increase between a one of the impedance values and an immediately preceding one of the impedance values, and
    trigger an alert providing notice of the sudden increase.

13. The system of claim 12, further comprising a pressure sensor configured to sense a pressure of fluid within the implantable restriction device over the period of time and to communicate pressure data to the impedance measuring device, wherein the impedance measuring device is configured to analyze the pressure data to determine if the pressure of fluid increased at a time corresponding to the one of the impedance values and the immediately preceding one of the impedance values, and if so, to allow the alert to be triggered, and if not, to not trigger the alert.

14. The system of claim 1, wherein the period of time is a plurality of days.

15. A restriction system for forming a restriction in a patient, comprising:
    an implantable measuring device configured to be in communication with an implantable restriction device configured to form a restriction in a patient, and to gather data related to a weight of the patient, the measuring device including at least two sensor electrodes disposed on a tissue-contacting surface of the implantable restriction device; and
    a controller configured to be in electronic communication with the sensor electrodes and to measure an impedance between the sensor electrodes over a period of time to gather a sequence of impedance values, and configured to signal for an adjustment of the patient's treatment concerning the implantable restriction device if the gathered data indicates an inflection regarding the weight of the patient,
    wherein the controller is configured to signal for the adjustment of the patient's treatment concerning the implantable restriction device if the sequence of impedance values indicates an inflection in a trend of the weight of the patient over the period of time and
    wherein the controller is configured to determine that the trend is weight loss of the patient if the sequence of impedance values indicates an asymptotic decrease in the impedance over the period of time, and to determine that the trend is weight gain of the patient if the sequence of impedance values indicates an asymptotic increase in the impedance over the period of time.

16. The system of claim 15, wherein the sensor electrodes are configured to be in contact with tissue proximate to the restriction formed by the implantable restriction device, and wherein the impedance measuring device is configured to measure the impedance of the tissue.

17. The system of claim 16, wherein the controller is configured to signal for a change of fluid volume within the implantable restriction device if the measured impedance falls within a range of impedance values.

18. The system of claim 15, wherein the controller is configured to analyze the gathered data for an inflection in a plot line indicating a minimization of a fat pad of the patient.

19. The system of claim 15, further comprising a pressure sensor configured to sense a pressure of fluid within the implantable restriction device and to communicate pressure data to the controller, wherein the controller is configured to use the pressure data to corroborate an inflection regarding the weight of the patient and to signal for an adjustment of the patient's treatment if so corroborated.

20. The system of claim 15, wherein the signal for an adjustment of the patient's treatment includes a signal to adjust an amount of fluid within the implantable restriction device.

21. The system of claim 15, wherein the signal for an adjustment of the patient's treatment includes a signal to modify the patient's treatment plan.

22. The system of claim 15, wherein the period of time is a plurality of days.

* * * * *